United States Patent
Hartmann et al.

(10) Patent No.: US 10,617,374 B2
(45) Date of Patent: Apr. 14, 2020

(54) METHOD AND APPARATUS FOR IMAGE-BASED NAVIGATION

(75) Inventors: Steven L. Hartmann, Superior, CO (US); Bruce M. Burg, Louisville, CO (US); Andrew Bzostek, Erie, CO (US); Brad Jacobsen, Erie, CO (US); Matthew W. Koenig, Dacono, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 0 days.

(21) Appl. No.: 13/016,740

(22) Filed: Jan. 28, 2011

(65) Prior Publication Data

US 2012/0197108 A1 Aug. 2, 2012

(51) Int. Cl.
| | |
|---|---|
| *A61B 5/00* | (2006.01) |
| *A61B 6/00* | (2006.01) |
| *H01F 5/00* | (2006.01) |
| *A61B 34/20* | (2016.01) |
| *A61B 90/00* | (2016.01) |

(52) U.S. Cl.
CPC .......... *A61B 6/4405* (2013.01); *A61B 34/20* (2016.02); *H01F 5/00* (2013.01); *A61B 2034/2051* (2016.02); *A61B 2090/397* (2016.02)

(58) Field of Classification Search
CPC .................................................. A61B 19/5244
USPC .......... 600/424; 324/207.11, 207.13, 207.15, 324/207.17
See application file for complete search history.

(56) References Cited

U.S. PATENT DOCUMENTS

| | | |
|---|---|---|
| 3,568,660 A | 3/1971 | Crites et al. |
| 4,188,979 A | 2/1980 | Nakamura et al. |
| 4,317,078 A | 2/1982 | Weed et al. |
| 4,788,987 A | 12/1988 | Nickel |
| 4,806,182 A | 2/1989 | Rydell et al. |
| 4,813,210 A | 3/1989 | Masuda et al. |
| 5,005,592 A | 4/1991 | Cartmell |
| 5,226,423 A | 7/1993 | Tenerz et al. |
| 5,391,199 A | 2/1995 | Ben-Haim |
| 5,443,489 A | 8/1995 | Ben-Haim |
| 5,538,511 A | 7/1996 | Van Antwerp |
| 5,591,141 A | 1/1997 | Nettekoven |

(Continued)

FOREIGN PATENT DOCUMENTS

| | | |
|---|---|---|
| AU | 2011245296 A1 | 12/2012 |
| CA | 2797359 A1 | 11/2011 |

(Continued)

OTHER PUBLICATIONS

"Mayfield® Skull Clamps and Headrest Systems," Mayfield® Surgical Devices Product Index, pp. 1-6, © 2004 Integra LifeSciences Corporation.

(Continued)

*Primary Examiner* — Rajeev P Siripurapu
(74) *Attorney, Agent, or Firm* — Harness Dickey

(57) ABSTRACT

A system and method for a procedure that can be performed on any appropriate subject. Procedures can include assembling any appropriate work piece or installing members into a work piece, such as an airframe, autoframe, etc. Regardless of the subject, tracking a substantially small tracking device in a plurality of degrees of freedom is provided. The tracking device can be positioned on or be formed in an instrument to be tracked.

43 Claims, 6 Drawing Sheets

(56) References Cited

U.S. PATENT DOCUMENTS

| | | |
|---|---|---|
| 5,592,939 A | 1/1997 | Martinelli |
| 5,645,559 A | 7/1997 | Hachtman et al. |
| 5,693,085 A | 12/1997 | Buirge et al. |
| 5,740,808 A | 4/1998 | Panescu et al. |
| 5,762,637 A | 6/1998 | Berg et al. |
| 5,840,024 A | 11/1998 | Taniguchi et al. |
| 5,913,820 A | 6/1999 | Bladen et al. |
| 5,938,602 A | 8/1999 | Lloyd |
| 5,963,120 A * | 10/1999 | Zaviska .................... 336/208 |
| 5,983,126 A | 11/1999 | Wittkampf |
| 6,010,529 A | 1/2000 | Herweck et al. |
| 6,021,343 A | 2/2000 | Foley et al. |
| 6,106,486 A | 8/2000 | Tenerz et al. |
| 6,201,387 B1 | 3/2001 | Govari |
| 6,235,038 B1 | 5/2001 | Hunter et al. |
| 6,253,770 B1 * | 7/2001 | Acker et al. .................... 128/899 |
| 6,254,600 B1 | 7/2001 | Willink et al. |
| 6,332,891 B1 | 12/2001 | Himes |
| 6,336,906 B1 | 1/2002 | Hammarstrom et al. |
| 6,348,058 B1 | 2/2002 | Melkent et al. |
| 6,381,485 B1 | 4/2002 | Hunter et al. |
| 6,427,079 B1 | 7/2002 | Schneider et al. |
| 6,434,507 B1 | 8/2002 | Clayton et al. |
| 6,474,341 B1 | 11/2002 | Hunter et al. |
| 6,478,802 B2 | 11/2002 | Kienzle, III et al. |
| 6,556,857 B1 | 4/2003 | Estes et al. |
| 6,610,066 B2 | 8/2003 | Dinger et al. |
| 6,615,155 B2 | 9/2003 | Gilboa |
| 6,616,651 B1 | 9/2003 | Stevens |
| 6,687,531 B1 | 2/2004 | Ferre et al. |
| 6,689,049 B1 | 2/2004 | Miyagi et al. |
| 6,695,764 B2 | 2/2004 | Silverman et al. |
| 6,747,539 B1 | 6/2004 | Martinelli |
| 6,796,988 B2 | 9/2004 | Melkent et al. |
| 6,833,814 B2 | 12/2004 | Gilboa et al. |
| 6,926,674 B2 | 8/2005 | Tenerz et al. |
| 6,940,941 B2 | 9/2005 | Gregerson et al. |
| 6,977,575 B2 | 12/2005 | Bernier |
| 6,980,849 B2 | 12/2005 | Sasso |
| 6,993,374 B2 | 1/2006 | Sasso |
| 7,001,045 B2 | 2/2006 | Gregerson et al. |
| 7,106,825 B2 | 9/2006 | Gregerson et al. |
| 7,108,421 B2 | 9/2006 | Gregerson et al. |
| 7,118,378 B1 | 10/2006 | Karapetyan |
| 7,135,978 B2 | 11/2006 | Gisselberg et al. |
| 7,153,308 B2 | 12/2006 | Peterson |
| 7,166,114 B2 | 1/2007 | Moctezuma De La Barrera et al. |
| 7,188,998 B2 | 3/2007 | Gregerson et al. |
| 7,226,456 B2 | 6/2007 | O'Neil et al. |
| 7,346,417 B2 | 3/2008 | Luth et al. |
| 7,366,562 B2 | 4/2008 | Dukesherer et al. |
| 7,410,480 B2 | 8/2008 | Muni et al. |
| 7,462,175 B2 | 12/2008 | Chang et al. |
| 7,500,971 B2 | 3/2009 | Chang et al. |
| 7,537,594 B2 | 5/2009 | Sartor |
| 7,559,137 B2 | 7/2009 | Beer et al. |
| 7,604,609 B2 | 10/2009 | Jervis |
| 7,625,617 B1 | 12/2009 | Anderson et al. |
| 7,629,015 B2 | 12/2009 | Anderson et al. |
| 7,637,896 B2 | 12/2009 | Voegele et al. |
| 7,647,083 B2 | 1/2010 | Al-Ali et al. |
| 7,657,301 B2 | 2/2010 | Mate et al. |
| 7,697,972 B2 | 4/2010 | Verard et al. |
| 7,751,865 B2 | 7/2010 | Jascob et al. |
| 7,763,035 B2 | 7/2010 | Melkent et al. |
| 7,774,933 B2 | 8/2010 | Wilson et al. |
| 7,797,032 B2 | 9/2010 | Martinelli et al. |
| 7,818,044 B2 | 10/2010 | Dukesherer et al. |
| 7,840,253 B2 | 11/2010 | Tremblay et al. |
| 7,844,319 B2 | 11/2010 | Susil et al. |
| 7,881,769 B2 | 2/2011 | Sobe |
| 7,971,341 B2 | 7/2011 | Dukesherer et al. |
| 7,979,032 B2 | 7/2011 | Lomnitz |
| 8,075,969 B2 | 12/2011 | Anderson et al. |
| 8,086,298 B2 | 12/2011 | Whitmore, III et al. |
| 8,105,339 B2 | 1/2012 | Melkent et al. |
| 8,147,486 B2 | 4/2012 | Honour et al. |
| 8,239,001 B2 | 8/2012 | Verard et al. |
| 8,251,949 B2 | 8/2012 | Warnack |
| 8,255,027 B2 | 8/2012 | Al-Ali et al. |
| 8,504,139 B2 | 8/2013 | Jacobsen et al. |
| 8,644,907 B2 | 2/2014 | Hartmann et al. |
| 8,648,605 B2 | 2/2014 | Nakamura et al. |
| 8,674,694 B2 | 3/2014 | Hyde et al. |
| 8,862,204 B2 | 10/2014 | Sobe et al. |
| 9,232,985 B2 | 1/2016 | Jacobsen et al. |
| 9,504,530 B2 | 11/2016 | Hartmann et al. |
| 9,623,208 B2 | 4/2017 | Wright et al. |
| 9,750,486 B2 | 9/2017 | Burg et al. |
| 2001/0034549 A1 | 10/2001 | Bartholf et al. |
| 2002/0153015 A1 | 10/2002 | Garibaldi et al. |
| 2002/0165448 A1 | 11/2002 | Ben-Haim et al. |
| 2002/0167313 A1 | 11/2002 | Taimisto |
| 2003/0009095 A1 | 1/2003 | Skarda |
| 2003/0050552 A1 | 3/2003 | Vu |
| 2003/0187347 A1 | 10/2003 | Nevo et al. |
| 2003/0216639 A1 | 11/2003 | Gilboa et al. |
| 2004/0097804 A1 | 5/2004 | Sobe |
| 2004/0116803 A1 | 6/2004 | Jascob et al. |
| 2004/0199072 A1 | 10/2004 | Sprouse et al. |
| 2004/0215071 A1 | 10/2004 | Frank et al. |
| 2005/0027339 A1 | 2/2005 | Schrom et al. |
| 2005/0027340 A1 | 2/2005 | Schrom et al. |
| 2005/0027341 A1 | 2/2005 | Schrom et al. |
| 2005/0060885 A1 | 3/2005 | Johnson et al. |
| 2005/0085715 A1 | 4/2005 | Dukesherer et al. |
| 2005/0085720 A1 | 4/2005 | Jascob et al. |
| 2005/0105212 A1 | 5/2005 | Sato |
| 2005/0137576 A1 | 6/2005 | Packard |
| 2005/0154294 A1 * | 7/2005 | Uchiyama et al. ............ 600/420 |
| 2005/0171508 A1 * | 8/2005 | Gilboa .......................... 604/528 |
| 2005/0215922 A1 | 9/2005 | Tsonton et al. |
| 2005/0222554 A1 | 10/2005 | Wallace et al. |
| 2006/0004286 A1 | 1/2006 | Chang et al. |
| 2006/0025677 A1 | 2/2006 | Verard et al. |
| 2006/0036189 A1 | 2/2006 | Martinelli et al. |
| 2006/0084867 A1 | 4/2006 | Tremblay et al. |
| 2006/0129061 A1 | 6/2006 | Kaneto et al. |
| 2006/0142656 A1 | 6/2006 | Malackowski et al. |
| 2006/0173284 A1 | 8/2006 | Ackerman et al. |
| 2006/0206039 A1 | 9/2006 | Wilson et al. |
| 2006/0206170 A1 | 9/2006 | Denker et al. |
| 2006/0224142 A1 | 10/2006 | Wilson et al. |
| 2006/0229624 A1 | 10/2006 | May et al. |
| 2006/0235314 A1 | 10/2006 | Migliuolo et al. |
| 2007/0032862 A1 | 2/2007 | Weber et al. |
| 2007/0088416 A1 | 4/2007 | Atalar et al. |
| 2007/0157828 A1 * | 7/2007 | Susel et al. ..................... 101/35 |
| 2007/0197899 A1 | 8/2007 | Ritter et al. |
| 2007/0208252 A1 | 9/2007 | Makower |
| 2007/0220746 A1 | 9/2007 | Anderson et al. |
| 2007/0225595 A1 | 9/2007 | Malackowski et al. |
| 2007/0255132 A1 | 11/2007 | Shalgi et al. |
| 2008/0097195 A1 | 4/2008 | Urquhart et al. |
| 2008/0097347 A1 | 4/2008 | Arvanaghi |
| 2008/0119727 A1 | 5/2008 | Barbagli et al. |
| 2008/0119919 A1 | 5/2008 | Atalar et al. |
| 2008/0132909 A1 | 6/2008 | Jascob et al. |
| 2008/0171934 A1 * | 7/2008 | Greenan ............... A61B 5/6857 |
| | | 600/411 |
| 2008/0171937 A1 | 7/2008 | Dukesherer et al. |
| 2008/0172069 A1 | 7/2008 | Dukesherer et al. |
| 2008/0228195 A1 | 9/2008 | von Jako et al. |
| 2009/0088728 A1 | 4/2009 | Dollar et al. |
| 2009/0118742 A1 | 5/2009 | Hartmann et al. |
| 2009/0171187 A1 * | 7/2009 | Gerhart et al. .............. 600/421 |
| 2009/0204023 A1 | 8/2009 | Goldenberg |
| 2009/0209947 A1 | 8/2009 | Gordin et al. |
| 2010/0063383 A1 | 3/2010 | Anderson et al. |
| 2010/0081965 A1 | 4/2010 | Mugan et al. |
| 2010/0130852 A1 | 5/2010 | Neidert et al. |
| 2010/0134096 A1 | 6/2010 | Chiba et al. |
| 2010/0185083 A1 | 7/2010 | Neidert et al. |
| 2010/0210939 A1 | 8/2010 | Hartmann et al. |

(56) References Cited

U.S. PATENT DOCUMENTS

| | | |
|---|---|---|
| 2010/0228117 A1 | 9/2010 | Hartmann |
| 2010/0234724 A1 | 9/2010 | Jacobsen et al. |
| 2010/0253361 A1 | 10/2010 | Nakamura et al. |
| 2010/0280363 A1 | 11/2010 | Skarda et al. |
| 2010/0331763 A1 | 12/2010 | Wilson et al. |
| 2011/0014705 A1 | 1/2011 | Leach et al. |
| 2011/0060214 A1 | 3/2011 | Makower |
| 2011/0066029 A1 | 3/2011 | Lyu et al. |
| 2011/0118592 A1 | 5/2011 | Sobe et al. |
| 2011/0251519 A1 | 10/2011 | Romoscanu |
| 2011/0258842 A1 | 10/2011 | Dukesherer et al. |
| 2011/0270081 A1 | 11/2011 | Burg et al. |
| 2012/0112746 A1 | 5/2012 | Hyde et al. |
| 2012/0172696 A1 | 7/2012 | Kallback et al. |
| 2012/0197109 A1 | 8/2012 | Hartmann et al. |
| 2012/0197110 A1 | 8/2012 | Hartmann et al. |
| 2012/0245665 A1 | 9/2012 | Friedman et al. |
| 2012/0271135 A1 | 10/2012 | Burke et al. |
| 2012/0283570 A1 | 11/2012 | Tegg |
| 2013/0066194 A1 | 3/2013 | Seter et al. |
| 2013/0137954 A1 | 5/2013 | Jacobsen et al. |
| 2013/0317355 A1 | 11/2013 | Jacobsen et al. |
| 2014/0012130 A1 | 1/2014 | Jacobsen et al. |
| 2014/0148692 A1 | 5/2014 | Hartmann et al. |
| 2014/0158555 A1 | 6/2014 | Nakamura et al. |
| 2014/0276004 A1 | 9/2014 | Strupeck et al. |
| 2015/0005625 A1 | 1/2015 | Sobe et al. |

FOREIGN PATENT DOCUMENTS

| | | |
|---|---|---|
| CN | 101621966 A | 1/2010 |
| CN | 103068332 A | 4/2013 |
| DE | 102009030731 A1 | 12/2010 |
| EP | 0425319 A2 | 5/1991 |
| EP | 1302172 A1 | 4/2003 |
| EP | 1510182 A2 | 3/2005 |
| EP | 1552795 A1 | 7/2005 |
| EP | 1658818 A1 | 5/2006 |
| EP | 1743591 A2 | 1/2007 |
| EP | 1806756 A2 | 7/2007 |
| EP | 2114263 A2 | 11/2009 |
| EP | 2123220 A1 | 11/2009 |
| EP | 2563260 A2 | 3/2013 |
| JP | 2000151041 A | 5/2000 |
| JP | 03-207344 B2 | 9/2001 |
| JP | 2006167119 A | 6/2006 |
| JP | 2007-527296 A | 9/2007 |
| JP | 2008-155033 A | 7/2008 |
| JP | 2008194475 A | 8/2008 |
| JP | 2010082446 A | 4/2010 |
| WO | WO-9632060 A1 | 10/1996 |
| WO | WO-9729682 A1 | 8/1997 |
| WO | WO-9729684 A1 | 8/1997 |
| WO | WO-9940856 A1 | 8/1999 |
| WO | WO-0038571 A1 | 7/2000 |
| WO | WO-0134050 A2 | 5/2001 |
| WO | WO-2006096685 A1 | 9/2006 |
| WO | WO-2006116597 A2 | 11/2006 |
| WO | 2008054423 A1 | 5/2008 |
| WO | WO-2008105874 A1 | 9/2008 |
| WO | WO-2009152486 A1 | 12/2009 |
| WO | WO-2010049834 A1 | 5/2010 |
| WO | WO-2010124285 A1 | 10/2010 |
| WO | WO-2010144419 A2 | 12/2010 |
| WO | WO-2011137301 A2 | 11/2011 |
| WO | WO-2012103304 | 8/2012 |
| WO | WO-2012103304 A1 | 8/2012 |
| WO | WO-2012103407 A1 | 8/2012 |
| WO | WO-2012103410 A1 | 8/2012 |
| WO | WO-2013062869 A1 | 5/2013 |

OTHER PUBLICATIONS

"Medtronic O-Arm Multi-Dimensional Surgical Imaging System"; Brochure, 24pp, 2009.

"StealthStation_S7_System® Information Center in the OR," (2009) Medtronic, Inc.

"StealthStation® TRIA™ plus Treatment Guidance System," brochure, Medtronic Surgical Navigation Technologies (2004) 2 pages.

"TREON, StealthStation," brochure, Medtronic Surgical Navigation Technologies (2001) 8 pages.

"InstaTrak 3500 Plus. Applications: ENT. Cranial." http://www.gehealthcare/usen/xr/surgery/products/nav.html (printed Dec. 14, 2009).

"InstaTrak™ 3500 plus—Cranial. Multi-application electromagnetic surgical navigation system for ENT, Cranial, and Spine procedures." GE Healthcare http://www.gehealthcare.com/euen/surgery/products/instatrak-3500-plus-cranial/index.html (printed Dec. 14, 2009).

"InstaTrak™ 3500 plus—ENT. Multi-application electromagnetic surgical navigation system for ENT and Cranial." GE Healthcare http://www.gehealthcare.com/euen/surgery/products/instatrak-3500-plus-ent/index.html (printed Dec. 14, 2009).

"InstaTrak® Image Guided Sinus Surgery, Introduction to the InstaTrak System." Sinus-Clear.com http:/www.sinus-clear.com/instatrak.htm (printed Dec. 14, 2009).

"The doctor can see you now" brochure. GE Medical Systems (2003) General Electric Company.

Acclarent™ "Instructions for Use. Balloon Sinuplasty™ System. Relieva™ Devices, ReliENT™ Navigation System, and OptiLINK™ Extension." (Aug. 21, 2009) pp. 1-13.

Acclarent™ "Instructions for Use. Relieva Flex™ Sinus Guide Catheter, Relieva® Sinus Guide Catheter." (Sep. 19, 2009) pp. 1-6.

International Preliminary Report on Patentability dated Nov. 15, 2012 for PCT/US2011/34475 claiming benefit of U.S. Appl. No. 13/097,243, filed Apr. 29, 2011.

International Search Report and Written Opinion dated Feb. 6, 2013 for PCT/US2012/061086 claiming benefit of U.S. Appl. No. 13/281,001, filed Oct. 25, 2011.

International Search Report and Written Opinion dated Jul. 6, 2012 for PCT/US2012/022840 claiming benefit to U.S. Appl. No. 13/016,762, filed Jan. 28, 2011.

International Search Report and Written Opinion dated May 9, 2012 for PCT/US2012/022676 claiming benefit of U.S. Appl. No. 13/016,740, filed Jan. 28, 2011.

International Search Report and Written Opinion dated May 9, 2012 for PCT/US2012/022846 claiming benefit of U.S. Appl. No. 13/016,765, filed Jan. 28, 2011.

International Search Report and Written Opinion dated Oct. 31, 2011, claiming benefit of U.S. Appl. No. 13/097,243, filed Apr. 29, 2011.

"Flexible electronics," Dec. 19, 2012 (Dec. 19, 2012), XP055112518, en.wikipedia.org. Retrieved form the Internet: <URL:http://en.wikipedia.org/w/index.php?title=Flexible_electronics&oldid=528841651> [retrieved on Apr. 7, 2014]. (6 sheets).

"Flexible Printed Circuit Manufacturer—Capabilities," Aug. 16, 2012 (Aug. 16, 2012), XP055112534, fpcexpress.com. Retrieved from the Internet: URL: <http://web.archive.org/web/20120816030431/http://fpcexpress.com/capabilities.html>. [retrieved on Apr. 7, 2014][retrieved on May 8, 2014]. (3 sheets).

"Minco Bulletin FC-3," Jul. 31, 2002 (Jul. 31, 2002). XP055115671, Retrieved from the Internet: <URL:http://www.temflexcontrols.com/pdf/fc3.pdf> [retrieved on Apr. 29, 2014]. (1 sheet).

"Sectional design standard for flexible printed boards," Internet Citation, Nov. 30, 1998 (Nov. 30, 1998), pp. 1-35, XP002691487, Retrieved form the Interent: <URL:http://222.184.16.210/smt/tzxt/bz/IPC-2223.pdf>. [retrieved on Feb. 1, 2013].

Examiner's Report dated Dec. 18, 2013 for Canadian Application No. 2,797,359 claiming benefit of U.S. Appl. No. 13/097,243, filed Apr. 29, 2011.

http://oxforddictionaries.com/definition/english/barrel (accessed Dec. 3, 2012).

International Preliminary Report on Patentability and Written Opinion dated May 8, 2014 for PCT/US2012/061086 claiming benefit of U.S. Appl. No. 13/281,001, filed Oct. 25, 2011.

(56) References Cited

OTHER PUBLICATIONS

International Preliminary Report on Patentability dated Aug. 8, 2013 for PCT/US2012/022676 claiming benefit of U.S. Appl. No. 13/016,740, filed Jan. 28, 2011.
International Preliminary Report on Patentability dated Aug. 8, 2013 for PCT/US2012/022840 claiming benefit of U.S. Appl. No. 13/016,762, filed Jan. 28, 2011.
International Preliminary Report on Patentability dated Aug. 8, 2013 for PCT/US2012/022846 claiming benefit of U.S. Appl. No. 13/016,765, filed Jan. 28, 2011.
International Search Report and Written Opinion dated Apr. 23, 2014 for PCT/US2014/012786 claiming benefit of U.S. Appl. No. 13/748,150, filed Jan. 23, 2013.
International Search Report and Written Opinion dated May 12, 2014 for PCT/US2014/012967 claiming benefit of U.S. Appl. No. 13/751,032, filed Jan. 25, 2013.
Japanese Office Action dated Jan. 7, 2014 for Japan Application No. 2013-508273 claiming benefit of U.S. Appl. No. 13/097,243, filed Apr. 29, 2011.
Chinese Office Action dated Sep. 3, 2014 for Chinese Application No. 201180031075.0 claiming benefit of PCT/US2011/034475 filed Apr. 29, 2011, claiming benefit from U.S. Appl. No. 61/330,024, filed Apr. 30, 2010 and U.S. Appl. No. 13/097,243, filed Apr. 29, 2011.
International Preliminary Report on Patentability and Written Opinion dated Sep. 22, 2011 for PCT/US2010/026655 claiming benefit of U.S. Appl. No. 12/400,451, filed Mar. 10, 2009.
International Search Report and Written Opinion dated Oct. 27, 2014 for PCT/US2014/028100 claiming benefit of U.S. Appl. No. 14/209,696, filed Mar. 13, 2014.
International Search Report dated Jul. 15, 2010 for PCT/US2010/026655 claiming benefit of U.S. Appl. No. 12/400,451, filed Mar. 10, 2009.
Invitation to Pay Additional Fees and Where Applicable, Protest Fee dated Aug. 14, 2014 for PCT/US2014/028100 claiming benefit of U.S. Appl. No. 14/209,696, filed Mar. 13, 2014.
Medtronic Navigation, "StealthStation® AXIEM™ Electromagnetic Navigation . . . ", 2005, www.stealthstation.com/physician/spine/library/axiem_ent.jsp, printed Aug. 19, 2006 (2 pages).
International Preliminary Report on Patentability and Written Opinion dated Aug. 6, 2015 for PCT/US2014/012786 claiming benefit of U.S. Appl. No. 13/748,150, filed Jan. 23, 2013.
Chinese Office Action dated Apr. 3, 2015 for Chinese Application No. 201180031075.0 claiming benefit of PCT/US2011/034475 filed Apr. 29, 2011, claiming benefit from U.S. Appl. No. 61/330,024, filed Apr. 30, 2010 and U.S. Appl. No. 13/097,243, filed Apr. 29, 2011.
International Preliminary Report on Patentability and Written Opinion dated Sep. 24, 2015 for PCT/US2014/028100 claiming benefit to U.S. Appl. No. 14/209,696, filed Mar. 13, 2014.
International Preliminary Report on Patentability dated Oct. 27, 2015 for PCT/US2014/034022 claiming benefit of U.S. Appl. No. 13/871,616, filed Apr. 26, 2013.
Chinese Office Action dated Feb. 4, 2017 for Chinese Application No. 2014800059516.
Chinese Office Action dated Mar. 9, 2017 for Chinese Application No. 201480004264.2.
European Office Action dated Mar. 1, 2017 for European Application No. 12709722.8.
Communication pursuant to Article 94(3) EPC dated Nov. 24, 2016 for European Application No. 107084790 corresponding to PCT/US2010-026655 claiming benefit of U.S. Appl. No. 12/400,951, filed Mar. 10, 2009.
Communication pursuant to Article 94(3) EPC dated Feb. 1, 2017 for European Application No. 117199331 corresponding to PCT/US2011/034475, filed Apr. 29, 2011.

Japanese Office Action dated May 19, 2017 for Japanese Application No. 2016-510697 corresponding to PCT/US2014/034022 which claims benefit of U.S. Appl. No. 13/871,616, filed Apr. 26, 2013.
Japanese Office Action dated Aug. 29, 2016 for JP Application No. 2015-555345 corresponding to PCT/US2014/012967 which claims benefit of U.S. Appl. No. 13/751,032, filed Jan. 25, 2013.
Japanese Office Action dated Sep. 13, 2016 for JP Application No. 2016-510697 corresponding to PCT/US2014/034022 which claims benefit of U.S. Appl. No. 13/871,616, filed Apr. 26, 2013.
Australian Office Action dated Aug. 22, 2017 in corresponding Australian Application No. 2014209323.
Chinese Office Action dated Aug. 29, 2017 in corresponding Chinese Application No. 201480005951.6.
Chinese Office Action dated Jun. 29, 2017 in corresponding Chinese Application No. 201480023678.X.
Communication pursuant to Article 94(3) EPC for European Application No. 12703208.4-1654 dated Apr. 24, 2015.
European Office Action dated Oct. 20, 2015 for European Application No. 127841781 claiming benefit of PCT/US2012/061086 filed Oct. 19, 2012.
European Office Action dated Apr. 13, 2017 in corresponding European Application No. 14706985.0.
European Office Action dated Apr. 13, 2017 in European Application No. 14721108.0 corresponding to PCT/US2014/028100 which claims priority to U.S. Appl. No. 14/209,696, filed Mar. 13, 2014 and U.S. Appl. No. 61/790,479, filed Mar. 15, 2013.
European Office Action dated Jun. 22, 2017 in corresponding European Application No. 14703512.5.
International Preliminary Report on Patentability and Written Opinion dated Aug. 6, 2015 for PCT/US2014/012786 claiming benefit of U.S. Appl. No. 13/748,150, filed Jan. 23, 2012.
International Preliminary Report on Patentability and Written Opinion dated Aug. 6, 2015 for PCT/US2014/012967 claiming benefit of U.S. Appl. No. 13/751,032, filed Jan. 25, 2013.
Japanese Office Action dated Jul. 3, 2017 in corresponding Japanese Application No. 2015-555278.
Chinese Office Action dated Oct. 30, 2017 in corresponding/related Chinese Application No. 201610206046.8.
Canadian Office Action dated Oct. 24, 2017 in corresponding/related Canadian Application No. 2,942,656.
Japanese Office Action dated Dec. 1, 2017 in corresponding/related Japanese Application No. 2016-510697.
European Office Action dated Nov. 23, 2017 in corresponding/related European Application No. 14721108.0.
Australian Office Action dated Sep. 27, 2017 in corresponding/related Australian Application No. 2014209251.
Chinese Office Action dated Sep. 25, 2017 in corresponding/related Chinese Application No. 201480004264.2.
European Office Action dated Nov. 9, 2017 in corresponding/related European Application No. 11719933.1.
European Office Action dated Mar. 19, 2018 in corresponding/related European Application No. 17208055.8.
Australian Office Action dated Apr. 10, 2018 in corresponding/related Australian Application No. 2014257385.
Chinese Office Action dated Mar. 23, 2018 in corresponding/related Chinese Application No. 201480023678.X.
European Office Action dated May 3, 2018 in corresponding/related European Application No. 14725316.5.
Office Action dated Mar. 15, 2019 in corresponding/related European Application No. 17208055.8.
Canadian Office Action dated Jul. 6, 2018 in corresponding/related Canadian Application No. 2,942,656.
Australian Office Action dated Sep. 21, 2018 in corresponding/related Australian Application No. 2014209251.
Extended European Search Report dated Sep. 9, 2019 in corresponding/related European Application No. 19179149.0.
Extended European Search Report, dated Sep. 20, 2019, in corresponding/related European Application No. 19171550.7.

\* cited by examiner

METHOD AND APPARATUS FOR IMAGE-BASED NAVIGATION

FIELD

The present disclosure is related to surgical procedures, and particularly to surgical procedures that are navigated or use computer assisted surgery for performing a surgical procedure.

BACKGROUND

This section provides background information related to the present disclosure which is not necessarily prior art.

A procedure can be performed on any appropriate subject. For example, a procedure can be performed on a patient to position an implant in the patient. Though procedures can also include assembling any appropriate work piece or installing members into a work piece, such as an airframe, autoframe, etc. Regardless of the subject, generally the procedure can have a selected result that is efficacious. The efficacious result may be the desired or best result for the procedure.

A procedure on a human patient can be a surgical procedure performed to insert an implant, such as a pedicle screw. The pedicle screw can be placed in the patient according to appropriate techniques, such as an open procedure where a surgeon can view the procedure. Also, procedures can include hole drilling, screw placement, vessel stent placement, deep brain stimulation, etc.

SUMMARY

This section provides a general summary of the disclosure, and is not a comprehensive disclosure of its full scope or all of its features.

A surgical procedure can be performed with a navigated instrument. The navigated instrument can have associated therewith, such as attached directly to or relative to a surgical instrument, a tracking device to track a location of the instrument. The tracking device can be interconnected directly, such as wrapped around or positioned around a portion of an instrument, or extend from a mounting device connected to the instrument. According to various embodiments, a surgical procedure can be performed using a small or low invasive instrument. A small or low invasive instrument, however, may require or benefit from a small tracking device associated with an instrument for tracking a location of the instrument while minimizing a space or volume consumed by the tracking device itself. Accordingly a tracking device can be provided that is wrapped around an axis of an instrument, embedded in a surface of an instrument, or positioned or embedded in an interior of an instrument to minimize a dimensional increase due to the inclusion of a tracking device. Such instruments may also be used for air frame assembly or small (e.g. robotic) system repair.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings. According to various embodiments, a tracking device can be attached or interconnected with various portions in a navigation system. For example, a tracking device can be wrapped around or integrated into a portion of an instrument, such as in a shaft of a stylet or on a shaft of a stylet. Alternatively, or in addition thereto, a tracking device can be formed separately and connected, such as with a connection member with an instrument to be tracked. Accordingly, an instrument can include a tracking device that is wrapped directly around or placed directly on a portion of the instrument or it can be separately interconnected with a portion of the instrument. For example, the tracking device can be clipped or passed over a portion of the instrument.

Figure 1:
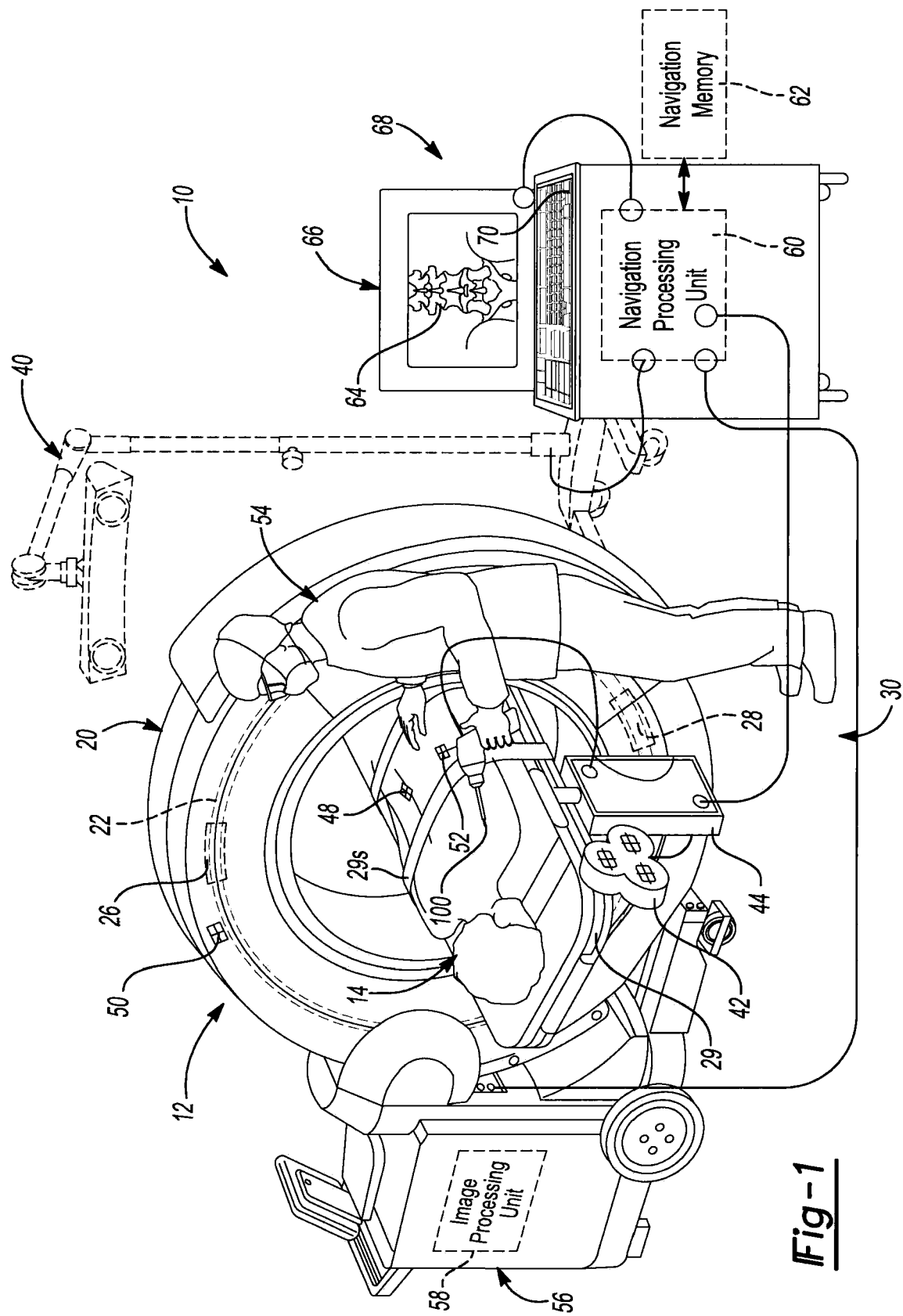
FIG. 1 is an environmental view of an operating theatre including an optional imaging system and a navigation system.

FIG. 1 is a diagram illustrating an overview of a navigation system 10 that can be used for various procedures. The navigation system 10 can be used to track the location of an item, such as an implant or an instrument (e.g. 100 as discussed herein), relative to a subject, such as a patient 14. It should further be noted that the navigation system 10 may be used to navigate any type of instrument, implant, or delivery system, including: guide wires, arthroscopic systems, orthopedic implants, spinal implants, deep brain stimulation (DBS) probes, etc. Non-human or surgical procedures may also use the instrument 100 and the navigation system 10. Moreover, the instruments may be used to navigate or map any region of the body. The navigation system 10 and the various tracked items may be used in any appropriate procedure, such as one that is generally minimally invasive or an open procedure.

The navigation system 10 can interface with or integrally include an imaging system 12 that is used to acquire pre-operative, intra-operative, or post-operative, or real-time image data of the patient 14. It will be understood, however, that any appropriate subject can be imaged and any appropriate procedure may be performed relative to the subject. In the example shown, the imaging system 12 comprises an O-arm® imaging device sold by Medtronic Navigation, Inc.

having a place of business in Louisville, Colo., USA. The imaging device 12 includes imaging portions such as a generally annular gantry housing 20 that encloses an image capturing portion 22. The image capturing portion 22 may include an x-ray source or emission portion 26 and an x-ray receiving or image receiving portion 28. The emission portion 26 and the image receiving portion 28 are generally spaced about 180 degrees from each other and mounted on a rotor (not illustrated) relative to a track of the image capturing portion 22. The image capturing portion 22 can be operable to rotate 360 degrees during image acquisition. The image capturing portion 22 may rotate around a central point or axis, allowing image data of the patient 14 to be acquired from multiple directions or in multiple planes.

The imaging system 12 can include those disclosed in U.S. Pat. Nos. 7,188,998; 7,108,421; 7,106,825; 7,001,045; and 6,940,941; all of which are incorporated herein by reference. The imaging system 12 can also include or be associated with various image processing systems, as discussed herein. Other possible imaging systems can include C-arm fluoroscopic imaging systems which can also be used to generate three-dimensional views of the patient 14. It is also understood that other appropriate imaging systems can be used such as magnetic resonance imaging (MRI), positron emission tomography imaging (PET), etc.

The patient 14 can be fixed onto an operating table 29, but is not required to be fixed to the table 29. The table 29 can include a plurality of straps 29s. The straps 29s can be secured around the patient 14 to fix the patient 14 relative to the table 29. Various apparatuses may be used to position the patient 14 in a static position on the operating table 29. Examples of such patient positioning devices are set forth in commonly assigned U.S. patent application Ser. No. 10/405,068, published as U.S. Pat. App. Pub. No. 2004-0199072 on Oct. 7, 2004, entitled "An Integrated Electromagnetic Navigation And Patient Positioning Device", filed Apr. 1, 2003 which is hereby incorporated by reference. Other known apparatuses may include a Mayfield® clamp.

The navigation system 10 includes a tracking system 30 that can be used to track instruments relative to the patient 14 or within a navigation space. The navigation system 10 can use image data from the imaging system 12 and information from the tracking system 30 to illustrate locations of the tracked instruments, as discussed herein. The tracking system 30 can include a plurality of types of tracking systems including an optical tracking system that includes an optical localizer 40 and/or an electromagnetic (EM) tracking system that can include an EM localizer 42 that communicates with or through an EM controller 44. The optical tracking system 40 and the EM tracking system with the EM localizer 42 can be used together to track multiple instruments or used together to redundantly track the same instrument. Various tracking devices, including those discussed further herein, can be tracked with the tracking system 30 and the information can be used by the navigation system 10 to allow for an output system to output, such as a display device to display, a position of an item. Briefly, tracking devices, such as a patient tracking device (to track the patient 14) 48, an imaging device tracking device 50 (to track the imaging device 12), and an instrument tracking device 52 (to track the instrument 100), allow selected portions of the operating theater to be tracked relative to one another with the appropriate tracking system, including the optical localizer 40 and/or the EM localizer 42.

It will be understood that any of the tracking devices 48-52 can be optical or EM tracking devices, or both, depending upon the tracking localizer used to track the respective tracking devices. It will be further understood that any appropriate tracking system can be used with the navigation system 10. Alternative tracking systems can include radar tracking systems, acoustic tracking systems, ultrasound tracking systems, and the like.

An exemplarily EM tracking system can include the STEALTHSTATION® AXIEM™ Navigation System, sold by Medtronic Navigation, Inc. having a place of business in Louisville, Colo. Exemplary tracking systems are also disclosed in U.S. Pat. No. 7,751,865, issued Jul. 6, 2010 and entitled "METHOD AND APPARATUS FOR SURGICAL NAVIGATION"; U.S. Pat. No. 5,913,820, titled "Position Location System," issued Jun. 22, 1999 and U.S. Pat. No. 5,592,939, titled "Method and System for Navigating a Catheter Probe," issued Jan. 14, 1997, all herein incorporated by reference.

Further, for EM tracking systems it may be necessary to provide shielding or distortion compensation systems to shield or compensate for distortions in the EM field generated by the EM localizer 42. Exemplary shielding systems include those in U.S. Pat. No. 7,797,032, issued on Sep. 14, 2010 and U.S. Pat. No. 6,747,539, issued on Jun. 8, 2004; distortion compensation systems can include those disclosed in U.S. patent Ser. No. 10/649,214, filed on Jan. 9, 2004, published as U.S. Pat. App. Pub. No. 2004/0116803, all of which are incorporated herein by reference.

With an EM tracking system, the localizer 42 and the various tracking devices can communicate through the EM controller 44. The EM controller 44 can include various amplifiers, filters, electrical isolation, and other systems. The EM controller 44 can also control the coils of the localizer 42 to either emit or receive an EM field for tracking. A wireless communications channel, however, such as that disclosed in U.S. Pat. No. 6,474,341, entitled "Surgical Communication Power System," issued Nov. 5, 2002, herein incorporated by reference, can be used as opposed to being coupled directly to the EM controller 44.

It will be understood that the tracking system may also be or include any appropriate tracking system, including a STEALTHSTATION® TRIA®, TREON®, and/or S7™ Navigation System having an optical localizer, similar to the optical localizer 40, sold by Medtronic Navigation, Inc. having a place of business in Louisville, Colo. Further alternative tracking systems are disclosed in U.S. Pat. No. 5,983,126, to Wittkampf et al. titled "Catheter Location System and Method," issued Nov. 9, 1999, which is hereby incorporated by reference. Other tracking systems include an acoustic, radiation, radar, etc. tracking or navigation systems.

The imaging system 12 can further include a support housing or cart 56 that can house a separate image processing unit 58. The cart can be connected to the gantry 20. The navigation system 10 can include a navigation processing unit 60 that can communicate or include a navigation memory 62. The navigation processing unit 60 can include a processor (e.g. a computer processor) that executes instructions to determine locations of the tracking devices 48-52 based or signals from the tracking devices. The navigation processing unit 60 can receive information, including image data, from the imaging system 12 and tracking information from the tracking systems 30, including the respective tracking devices 48-52 and the localizers 40-42. Image data can be displayed as an image 64 on a display device 66 of a workstation or other computer system 68 (e.g. laptop, desktop, tablet computer which may have a central processor to act as the navigation processing unit 60 by executing instructions). The workstation 68 can include appropriate input devices, such as a keyboard 70. It will be understood that other appropriate input devices can be included, such as a mouse, a foot pedal or the like which can be used separately or in combination. Also, all of the disclosed processing units or systems can be a single processor (e.g. a single central processing chip) that can execute different instructions to perform different tasks.

The image processing unit 58 processes image data from the imaging system 12 and transmits it to the navigation processor 60. It will be further understood, however, that the imaging system 12 need not perform any image processing and it can transmit the image data directly to the navigation processing unit 60. Accordingly, the navigation system 10 may include or operate with a single or multiple processing centers or units that can access single or multiple memory systems based upon system design.

In various embodiments, the imaging system 12 can generate image data that can be registered to the patient space or navigation space. In various embodiments, the position of the patient 14 relative to the imaging system 12 can be determined by the navigation system 10 with the patient tracking device 48 and the imaging system tracking device 50 to assist in registration. Accordingly, the position of the patient 14 relative to the imaging system 12 can be determined.

Alternatively, or in addition to tracking the imaging system 12, the imaging system 12, such as the O-arm® imaging system, can know its position and be repositioned to the same position within about 10 microns. This allows for a substantially precise placement of the imaging system 12 and precise determination of the position of the imaging device 12. Precise positioning of the imaging portion 22 is further described in U.S. Pat. Nos. 7,188,998; 7,108,421; 7,106,825; 7,001,045; and 6,940,941; all of which are incorporated herein by reference.

Subject or patient space and image space can be registered by identifying matching points or fiducial points in the patient space and related or identical points in the image space. When the position of the imaging device 12 is known, either through tracking or its "known" position (e.g. O-arm® imaging device sold by Medtronic, Inc.), or both, the image data is generated at a precise and known position. This can allow image data that is automatically or "inherently registered" to the patient 14 upon acquisition of the image data. Essentially, the position of the patient 14 is known precisely relative to the imaging system 12 due to the accurate positioning of the imaging system 12. This allows points in the image data to be known relative to points of the patient 14 because of the known precise location of the imaging system 12.

Alternatively, manual or automatic registration can occur by matching fiducial points in image data with fiducial points on the patient 14. Registration of image space to patient space allows for the generation of a translation map between the patient space and the image space. According to various embodiments, registration can occur by determining points that are substantially identical in the image space and the patient space. The identical points can include anatomical fiducial points or implanted fiducial points. Exemplary registration techniques are disclosed in Ser. No. 12/400,273, filed on Mar. 9, 2009, incorporated herein by reference.

Once registered, the navigation system 10 with or including the imaging system 12, can be used to perform selected procedures. Selected procedures can use the image data generated or acquired with the imaging system 12. Further, the imaging system 12 can be used to acquire image data at different times relative to a procedure. As discussed herein, image data can be acquired of the patient 14 subsequent to a selected portion of a procedure for various purposes, including confirmation of the portion of the procedure.

With continuing reference to FIG. 1, the imaging system 12 can generate actual three dimensional images of the patient 14 or virtual three dimensional images based on the image data, which can be registered to the patient/navigation space. The patient 14 can be placed relative to the imaging system 12 to allow the imaging system 12 to obtain image data of the patient 14. To generate 3D image data, the image data can be acquired from a plurality of views or positions relative to the patient 14. The 3D image data of the patient 14 can be used alone or with other information to assist in performing a procedure on the patient 14 or an appropriate subject. It will be understood, however, that any appropriate imaging system can be used, including magnetic resonance imaging, computed tomography, fluoroscopy, etc.

As generally illustrated in FIG. 1, the navigation system 10 can be used to navigate the instrument 100 relative to the patient 14. The navigation can be imageless (e.g. only illustrating icons at tracked locations of different tracked portions) or with images. Images can include acquired images (e.g. with the imaging system 12 or atlas images). Regardless, icons with or without images can be displayed on the display device 66. The tracking system 30 can track the instrument 100 and the navigation processing unit 60 can be used to determine the location of the instrument 100 and display the location of the instrument on the display 66 relative to the image 64 or, as mentioned above, without the image 64. Accordingly, according to various embodiments, such as those discussed herein, the user 54 can view an icon representing a location of the instrument 100 relative to the patient 14 or a selected portion of the patient 14 with or without images on the display 66. In so viewing the icons the user 54 can know the location of the instrument 100 in subject/patient space based upon the tracked location of the instrument 100 in image space.

The tracking device 52 can include various features, such as those discussed herein. In an EM tracking system 30 the tracking device 52 can include one or more coils that can either transmit an EM field or sense an EM field to generate a tracking signal (also referred to as an EM signal) to allow the navigation system 10 to determine the location of the tracked instrument 100 in the navigation space. The coils of the tracking device 52 can be formed as a wire wrapped around a core (e.g. formed of a solid material or air) or axis that can sense the magnetic field by generating a current within the wire or transmit an EM field that can be sensed by a sensing or localizer coil. The tracking device 52 can be formed directly on a device, as illustrated below, or, according to various embodiments, be connected to the instrument 100 to be tracked, as illustrated in FIG. 1.

Figure 2:
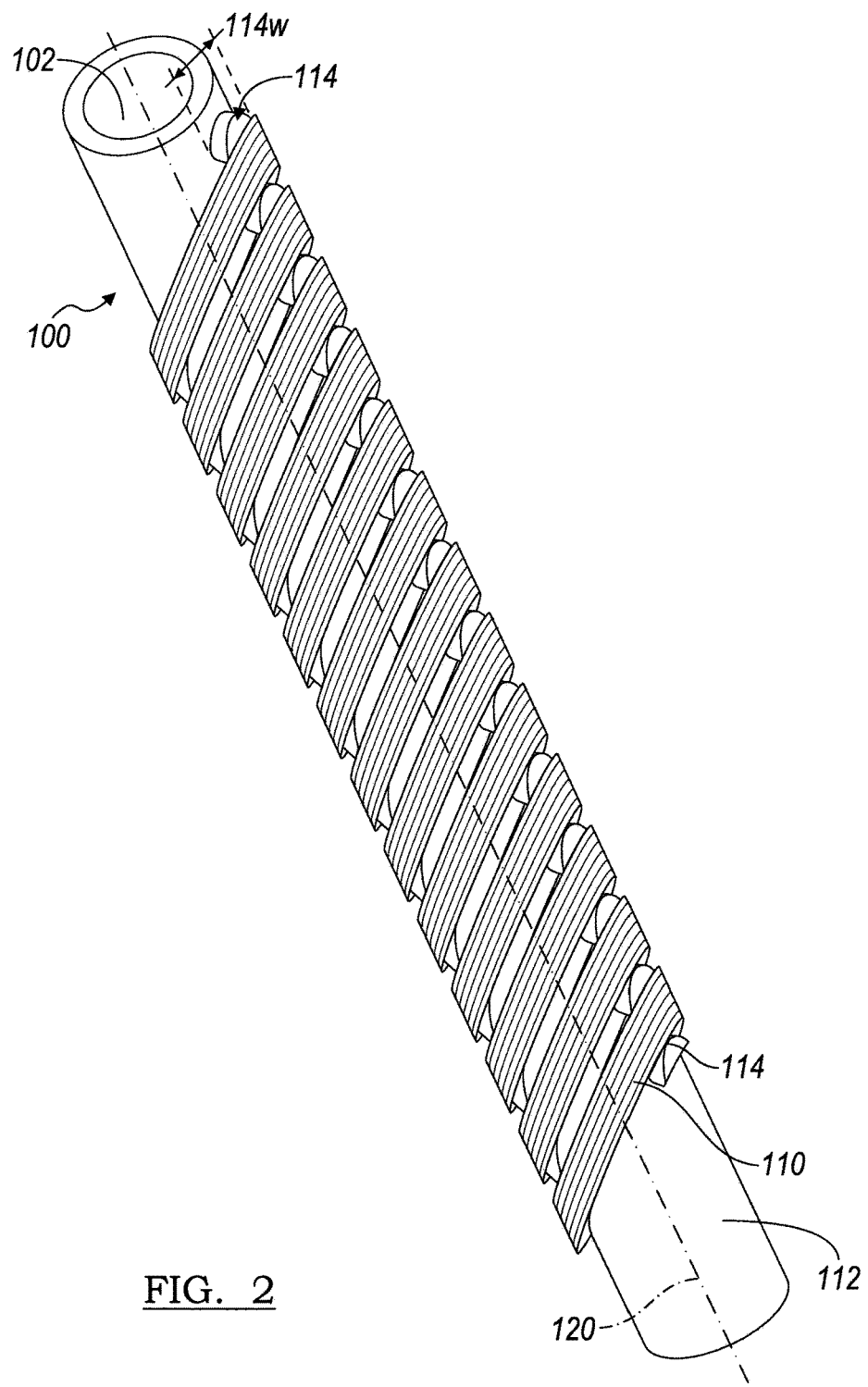
FIG. 2 is a perspective view of a tracking device on an instrument, according to various embodiments.
Figure 3:
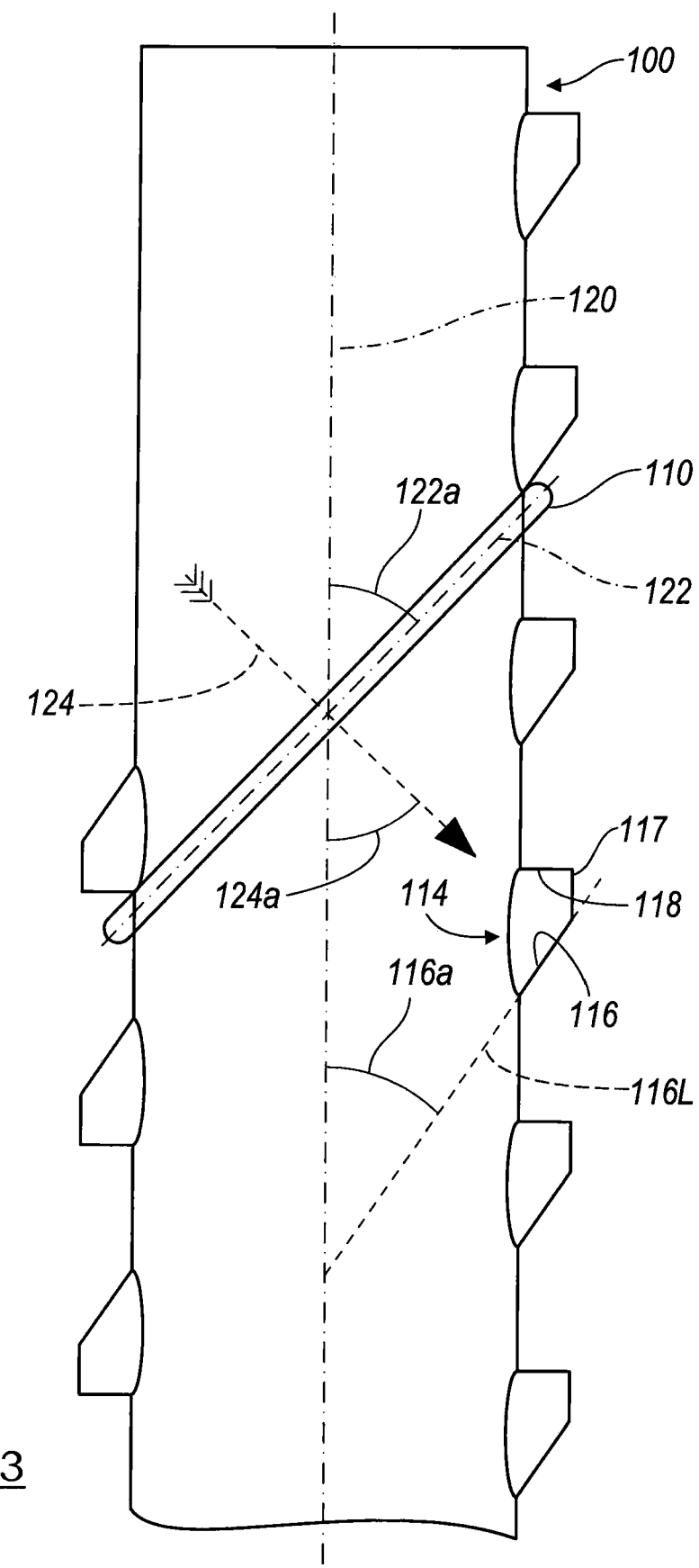
FIG. 3 is a detail perspective view of the tracking device of FIG. 2 on an instrument, according to various embodiments.

As discussed above in relation to FIG. 1, the navigation system 10 can include the various localizers 40, 42 relative to respective tracking devices 52 associated with the instrument 100, which can be a guide tube. The instrument 100, as illustrated in FIGS. 2-3, can be any appropriate instrument as exemplarily illustrated as a guide tube including a cannula or bore 102 extending along a length of the guide tube 100. It will be understood, however, that the instrument 100 can also include or be formed as a drill bit, a probe, or any other appropriate instrument. Additionally, the guide tube 100 can be substantially solid or itself designed as the tracking device 52 that can be associated with other instruments to be navigated with the navigation system 100.

The tracking device 52 is formed as a plurality of winds of wire 110 formed around an exterior or on an exterior wall 112 of the instrument 100 to form a coil. The winds or turns of wire 110 are formed between guide posts 114 and can include a plurality of guide posts 114 that are formed or positioned at selected positions on the external wall 112 of the guide tube 100. There may be a plurality of turns of the wire 110 between each guide post (e.g. FIG. 2) or there may be one turn of the wire 110 between each guide post (e.g. 144, FIG. 9). The wire can be insulated so that it is insulated from the instrument 100 and the next turn of the wire. It will also be understood that a portion including the coil of wire can be connected to the instrument to perform as the tracking device 52. For example, a sleeve with the coil of wire can be fit over an outer wall of the instrument 100.

With additional reference to FIG. 3, the guide posts 114 can extend from the external wall 112 to a height above the external wall 112. Alternatively, the posts 114 can be understood to define a maximum diameter of the instrument 100 and the wire 110 is wound, at least initially, within the maximum diameter. In other words, the wire 110 can be maintained below the height of the posts 114 or can be wound over top of the posts 114. The posts 114, however, may provide the greatest degree of guiding or support for the wire 110 when the wire 110 is between and below an outer edge of the posts 114.

The guide posts 114 are formed on the instrument 100 can include a slanted or guiding wall 116 and a support or second wall 118. Both the guide wall 116 and the support wall 118 can extend to an outer wall 117. The outer wall 117 can define an outer diameter or perimeter of the instrument 100. The posts 114 can also define a width 114w. The width 114w can be selected to engage the wire 110 in a manner to selectively hold the wire 110 or to cover a selected expanse of the instrument outer wall 112. Also, the posts 114 can be formed separately and adhered or fixed to the outer wall 112 (e.g. with adhesives, welding, threaded engagement) or can be formed as a single piece with the outer wall 112 (e.g. molding or machining the posts 114 from the outer wall 112).

The guide wall 116 has a surface that can extend along a plane or line 116l that extends at an angle 116a relative to a long axis 120 of the guide tube 100. The guide wall 116 can be the entire width 114w of the post or can be a selected portion thereof. It will also be understood, however, that the guide wall 116 need not be angled. For example, when a first post 114 is formed on the instrument and a second post 114 is formed on the instrument the first and second post can be axially positioned relative to one another such that when the wire 110 is wound the instrument 100 the wire 110 will achieve a selected angle to form the navigation vector, as discussed herein.

It will be understood that the long axis 120 can be a long axis of any appropriate instrument. Generally, the long axis 120 is substantially aligned with an end or length of the instrument 100 such that the long axis 120 substantially defines a line or trajectory of the instrument 100. Also, a second instrument may pass through the tube 100 the instrument, such as a needle, generally along the long axis 120 and through an end of a guide tube 100. Thus, the long axis 120 generally defines a long axis or real trajectory of an instrument or a portion being guided through a guide portion of an instrument relative to a subject. The long axis 120, however, may be any axis of the instrument 100 and may only be aligned with a long axis of the instrument 100. It will be understood, however, that the instrument need not be rigidly straight, but can be bent, curved, flexible, or otherwise moveable. Thus, the long axis 120 may refer to a long axis of a selected portion of the instrument 100 that may not be continuous for an entire length of the instrument 100.

The angle 116a can be selected from any appropriate angle. Generally, however, the angle 116a will be about 5 degrees to about 80 degrees, including about 10 degrees to about 80 degrees, and further including about 35 degrees to about 40 degrees relative to the long axis 120. As discussed in U.S. patent application Ser. No. 12/770,181 filed on Apr. 29, 2010 and published as U.S. Pat. App. Pub. No. 2010/0210939 on Aug. 19, 2010, incorporated herein by reference, providing an angle between a wrapped winding or coil of wire relative to the long axis 120 can provide for forming a tracking device relative to the instrument 100 that can determine an orientation or position of the instrument in multiple degrees of freedom. It is understood, as disclosed herein, having multiple coils at various angles relative to one another can increase the degrees of freedom tracking information (e.g. three dimensional position information and three degrees of orientation information, which can include yaw, pitch, and roll of the instrument). For example, one coil of wire can generally provide five degrees of freedom of location information (e.g. three position degrees and two orientation degrees). An additional coil affixed to a single device (e.g. the instrument 100) can be used to solve for six degree of freedom location information including three position degrees and three orientation degrees for a single instrument. Additional coils (e.g. three or more total coils) can be provided or used for redundancy and increased information for location determination of the instrument. Generally, location is understood to include both position and orientation information.

Figure 4:
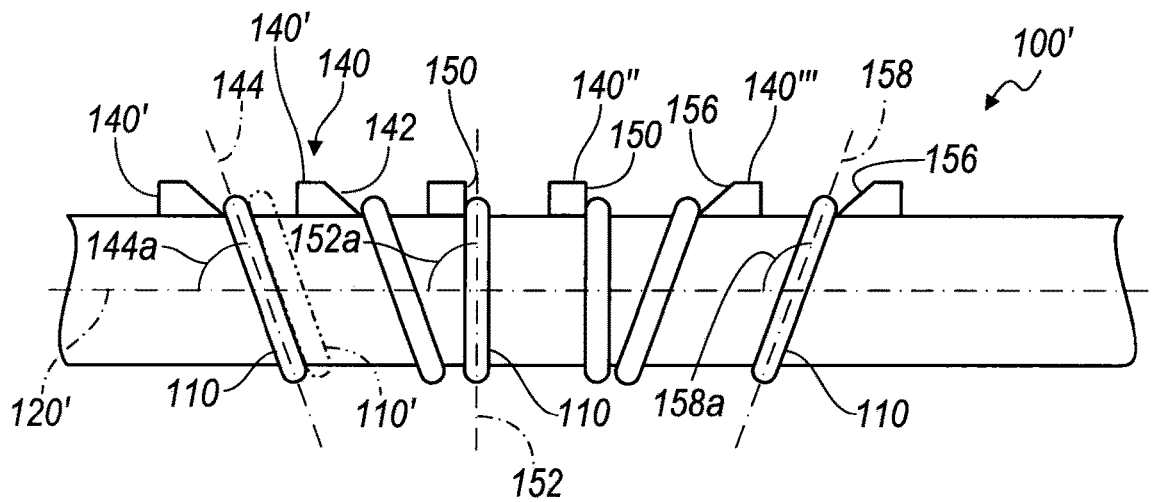
FIG. 4 is a plan view of a tracking device on an instrument, according to various embodiments.

As illustrated in FIG. 2, the coil winding 110 can include one or multiple wires. The coil winding can also include a single wire that is wound multiple times around the instrument and to engage the angled surface 116. Accordingly, a winding angle of the wire 110 can be defined along the axis or a line 122 and generally defines an angle 122a that is similar to the angle 116a defined by the guide wall 116 relative to the long axis 120. The angle 122a is achieved by contacting the wire 110 against the guide wall 116 as the wire 110 is being wound around the instrument 100. By contacting the guide wall 116, the wire 110 can be guided and maintained at the selected angle 122a relative to the long axis 120 of the instrument 100. It will be understood that if multiple windings are used next to each of the posts 114 then each successive winding may contact the previous wind of wire and not the angled wall 116 directly, as illustrated in FIG. 4.

Also, as illustrated in FIG. 3, the posts 114 can be positioned around the instrument 100, such as on opposed sides. However, it will be understood, that the posts 114 can be positioned at various offsets around the instrument 100. For example, the posts 114 can be positioned 45 degrees from each other around the instrument 100 and displaced axially for each successive post 114. Moreover, positioning the posts 114 displaced axially along the instrument 100 can allow for achieving the angle 122a without the angled wall 116. As illustrated in FIG. 3, the wire 110 can be wound to contact an axially displaced post 114 to achieve the angle 122a.

The angled wall 116 can also be provided to assist in the angle 122a creation or initiation, as illustrated in FIG. 3. In addition, the angled wall can assist in creating clearance for winding of the wire 110. For example, the angle between the top surface 117 and the wall 116 reduces or eliminates a snag or catch point (e.g. the corner created by a right angle between the walls) for the wire 110. Also, the angled wall allows for tight winding of additional layers of wires laid on the first or previous winding layer.

The selected angle 122*a*, as discussed herein, allows for the generation of a navigation vector 124 that is at an angle 124*a* relative to the long axis 120 and complementary to the angle 122*a*. The navigation vector 124 can generally be defined with the navigation system 10 by sensing a magnetic field with the tracking device 52 (e.g. having a current induced in the tracking device) defined by the plurality of windings 110 of wire or by emitting a field from the tracking device 52 to be sensed by the localizer 42. In other words, the navigation vector is defined in part by the position of the tracking device, but the vector is defined when used with the navigation system 10 by sensing the magnetic field or emitting a magnetic field. Regardless, the navigation vector 124 generally defines the angle 124*a* relative to the long axis 120 as disclosed in U.S. Pat. App. Pub. No. 2010/0210939.

With additional reference to FIG. 4, it will be understood that a single or a plurality of windings can be provided on the instrument 100, according to various embodiments. For example, as illustrated in FIG. 4, according to various embodiments an instrument 100' can include a plurality of guide posts 140 associated with the instrument 100'. A first number or a plurality of the guide posts 140' can include or have a first angled wall 142 that directs or causes the windings of the wire 110 to be formed relative to a long axis 120' of the instrument 100 along an axis 144 thus forming an angle 144*a* relative to the long axis. The first angle or angle 144*a* can be an acute angle relative to the long axis 122'. Also, a plurality of windings, such as at least a second winding 110', can be provided between each post 140'. A second portion or plurality of the guide post 140 can include the guide posts 140" that have a second guide wall 150 that will cause or form the wire 110 to be wrapped along an axis 152 relative to the long axis 120' of the instrument 100 and form an angle 152*a* relative to the long axis 120'. The angle 152*a* can generally be an angle different than the angle 144*a* and can include a substantially 90 degree angle relative to the long axis 120. Finally, a plurality of the guide posts 140 can include the posts 140''' and include a guide wall 156 that would cause the winding of the wire 110 to be formed along an axis 158 to form an angle 158*a* relative to the long axis 120'. The fifth angle 158*a* can generally be an angle different than the angle 144*a* and the angle 152*a* and generally, as illustrated, be an obtuse angle relative to the long axis 120'. It will be understood that each of the different coils can be at substantially orthogonal angles relative to one another, but is not required. Also, as discussed above three coils is not required for six degree of freedom location information.

As illustrated in FIG. 4, a plurality of tracking device portions can be used to form the tracking device 52. The tracking device portions can include windings of the wire 110 that are formed at a plurality of angles, such as three angles, relative to the long axis 120' of the instrument 100'. Each of the different windings that are at different angles relative to the long axis 120' can be substantially separated or insulted from one another to allow for the generation of three discreet signals. This can allow for the determination of three discreet navigational axis relative to the instrument 100' as disclosed in U.S. Pat. App. Pub. No. 2010/0210939. In allowing for the generation of three discreet signals, three discreet navigational axes are determined for each of the different angles of the windings relative to the long axis 120' of the instrument 100'. This can allow for the determination of a plurality of degrees of freedom due to tracking the three discreet angles or three discreet portions at a different orientations relative to the long axis 120' of the instrument 100'. It will be understood that any appropriate number of discreet angle portions can be made relative to the instrument 100' and three is merely exemplarily.

Figure 5A:
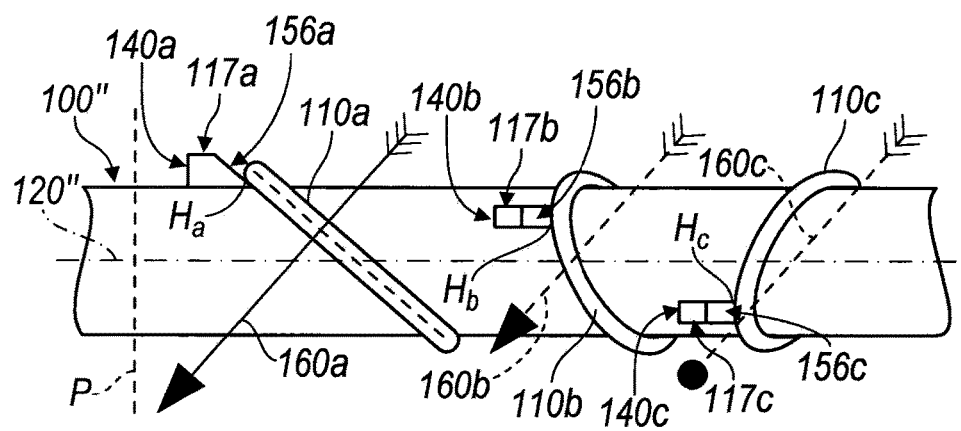
FIG. 5A is a plan view of a tracking device on an instrument, according to various embodiments.

In addition or alternatively to having the wire wrapped to form a plurality, such as three angles, as illustrated in FIG. 4, a plurality of different angles can be formed by rotating the navigation vectors relative to the long axis 120", as illustrated in FIG. 5A. The long axis 120" is defined by an instrument 100", which can be the same or different than the instruments discussed above. The instrument 100" can include one or more guide posts 140*a*, 140*b*, and 140*c* spaced apart axially along the length of the instrument 100". Additionally, each of the guide posts is rotated around the long axis 120" of the instrument, as further illustrated in FIG. 5B. Angles between each the guide posts 140*a*, 140*b*, 140*c* can be an appropriate angle, such as about 90-150 degrees, including about 100 degrees to about 150 degrees, and further including about 120 degrees (as exemplary illustrated by one of angles RA1, RA2, or RA3).

Figure 5B:
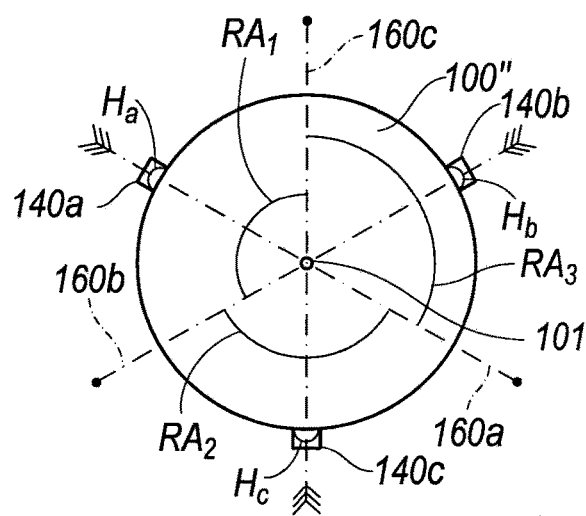
FIG. 5B is an end plan view the tracking device on an instrument illustrated in FIG. 5A.

With reference to FIGS. 5A and 5B, the instrument 100", can include at least three tracking devices or portions 110*a*, 110*b*, and 110*c*. Each of the tracking devices 110*a*, 110*b*, and 110*c* positioned on the instrument 100" can include or define a navigation vector 160*a*, 160*b*, and 160*c*. Therefore, the first navigation vector 160*a* can be formed by a first tracking device 110*a*, the second navigation vector 160*b* can be formed by the second tracking device 110*b*, and the third navigation vector 160*c* can be formed by the third tracking device 110*c* relative to the instrument 100". Each of the navigation vectors 160*a*, 160*b*, and 160*c* can be formed relative to the instrument 100" due to the positioning of the windings of material of the respective tracking devices 110*a*, 110*b*, and 110*c* at the winding angle relative to the instrument 100".

FIG. 5B attempts to illustrate on a two-dimensional plane of a page a three-dimensional rotation of angles of the three different windings of the wire 110*a*, 110*b*, and 110*c*. As discussed above, in relation to FIG. 4, each of the windings can be wound at the winding angle relative to the long axis 120' of the instrument 100'. As illustrated in FIGS. 5A and 5B, however, rather than having the windings formed at various and different winding angles relative to the long axis 120" of the instrument 100", each of the windings 110*a*, 110*b*, and 110*c* can be formed at substantially a single winding angle, including those winding angles discussed above and such as about 20 degrees to about 70 degrees, relative to the long axis 120" of the instrument 100".

Because each of the coils of the tracking device windings 110*a*, 110*b*, and 110*c* are at the same winding angle, to resolve the six degrees of freedom of location a top or high point Ha, Hb, Hc of each of the coil windings 110*a*, 110*b*, and 110*c* are rotated rotation angles $RA_1$, $RA_2$, and $RA_3$, such as about 120 degrees relative to one another, around the long axis 120" of the instrument 100". As discussed above, however, three windings are not required and an appropriate number of windings (e.g. only two windings 140*a* and 140*b*) can be used with an appropriate number of localizer coils. The rotation angles RA1, RA2, and RA3, can be selected to be 120 degrees to place each of the tops Ha, Hb, Hc substantially equidistant apart around the long and central axis 120" of the instrument 100". It will be understood, however, that the rotation angles $RA_1$, $RA_2$, and $RA_3$ can be about 90 degrees to about 180 degrees, including about 120 degrees. The at different rotation angles a distance about the long axis 120" between each of the vectors 160*a*-160*c* and/or the posts 140*a*-140*c* will also vary.

As illustrated in FIG. 5B, the front or top end of the windings Ha-Hc are all in substantially the same direction, such as towards a distal end of the instrument 100". Each of the windings 110a-110c are, thus, rotationally spaced apart around the center long axis 120" of the instrument 100". In this way, the navigation vectors 160a-160c for each of the windings 110a-110c can be formed at the same winding angle relative to the long axis 120" of the instrument 100". The navigation vectors 160a-160c are also, due to the rotational spacing of the coil windings tops Ha-Hc, rotationally spaced around the long axis 120".

The different navigation vectors 160a-160c are defined relative to a center 101 of the instrument 100". Each of the vectors 160a-160c can point towards a plane P, as illustrated in FIG. 5A, which is the plane of the page in FIG. 5B. The tails of the vectors 160a-160c can go into and past the plane on the page, thus all of the navigation vectors 160a-160c are not coplanar, but they all intersect the single plane P. Each of the vectors 160a-160c can be formed relative to the plane P rotationally spaced at the rotation angles relative to one another around the center 101 of the instrument 100".

As discussed above, the navigation vector angle can be selected by forming the windings of the tracking device 110a-110c at a selected angle relative to the long axis of the coil winding 110a-110c which can also be the long axis of the instrument 120". By changing the positioning of the angle of the rotation of the windings of the various tracking devices, the navigation vectors can be positioned relative to the instrument 100" in this selected manner. In various embodiments, the vectors 160a-160c are differently oriented relative to the instrument 100" by having more than one coil wound at the same winding angle, but being spaced relative to one another with the rotation angles.

The guide posts 140a-140c can be similar to those discussed above, but spaced axially along the axis 120" of the instrument 100". Thus, each of the guide posts can include top walls 117a-117c and angled walls or guide walls 156a-156c. Each of the angled walls can have the same angle as each of the coils 110a-110c can have the same angle. However, the guide posts 140a-140c positioned at varying rotational positions around the long axis 120" allows for the formation of different navigation vectors 160a-160c relative to the long axis 120" of the instrument 100".

Also, each of the coil portions 110a, 110b, 110c can be formed on separate members and interconnected for a use. For example, each of the coils could be formed on separated hollow members are that can be placed over the instrument 100" or over another hollow member. Each of the member can include an index finger and an index groove to ensure that the respective navigation vectors 160a-160c would be defined at the selected angle relative to one another. Thus, each of the coils 110a, 110b, and 110c need not be formed on the same or rigid member.

Figure 6:
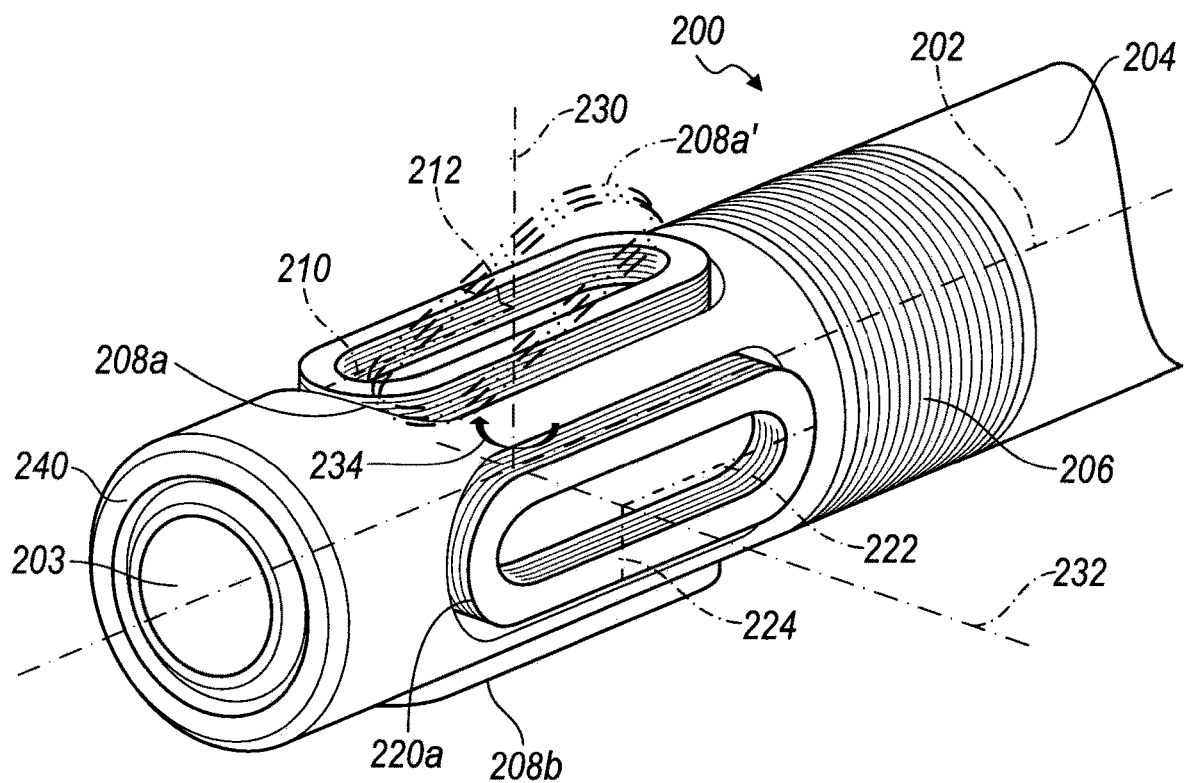
FIG. 6 is a perspective view of a tracking device on an instrument, according to various embodiments.

With reference to FIG. 6, the instrument, according to various embodiments is illustrated as an instrument 200. Instrument 200 can extend along a long axis 202 and define an internal cannula or bore 203. Accordingly, the instrument 200 can include an external wall 204 which can be inserted into a subject, such as the patient 14. The instrument 200 can be a guide tube or other guide instrument through which a second instrument, such as a drill bit or needle, is passed and guided. Alternatively, or in addition thereto, it will be understood that the instrument 200 may be solid, hollow, or cannulated and exemplarily be a drill bit, a probe, or other appropriate instrument. Accordingly, the exemplarily instrument 200 is merely for illustration for the current discussion.

The instrument 200 can include the tracking device 52 associated with the instrument 200. The tracking device 52 can include various portions that are operable in the navigation system 10 to allow for the determination of a location (including position and orientation) of the instrument 200. Generally, location information can include X, Y and/or Z dimensional coordinates along with at least two orientation coordinates (and when 6 degrees of freedom are determined at least three orientation coordinates). As discussed above, two separate coils can be used to solve for six degrees of freedom location information.

The tracking device 52 can be selected to include three sets of coils, although more or fewer coils can be selected based on the amount of location information selected. Each set of coils or coil can include a plurality of windings of a wire that can generate or be used to determine a navigation vector separate from the other coils or windings of wire. Accordingly, the navigation or tracking device 52 can include a first coil of wire 206 wound around a surface of the outer wall 204 or embedded in the surface of the outer wall 204 of the instrument 200. The wire of the coil 206 is generally insulated both from adjacent turns of the wire and from the instrument 200. Generally, the first coil 206 is wound around the long axis 202 and substantially coaxial therewith. Accordingly, the first coil 206 can define a navigation vector that generally aligned with the long axis 202 of the instrument 200. It will be understood, however, that the first winding need not be coaxial with the long axis 202.

A second coil set can include coil portions 208a and 208b. The coil portions 208a, b generally includes two coils that can be formed of a wire wound in a selected shape, such as an oval, circle, or ellipses, around a winding axis. The wire can be generally flat wire or a wire that has a round cross-section. As illustrated, the wire is wound in an oval having a long or major radius 210 generally along or aligned with the long axis 202 of the instrument 200, wherein the major radius 210 extends from a focus of the respective coil portion 208a,b to an edge of the respective coil portion 208a,b. The coil portion 208a also has a short or minor radius 212 generally perpendicular from the long radius 210 of the respective coil portions 208a or 208b, wherein the minor radius 212 also extends from the focus of the respective coil portion 208a,b towards an edge thereof. The coil portions 208a and 208b can be connected in series and positioned about 180 degrees from one another around the surface of the outer wall 204 of the instrument 200 and around the long axis 202.

Again, the coil portions 208a and 208b are generally positioned on the outer wall 204 or positioned at or in a holding region, for example in a depression in the outer wall 204 of the instrument 200. The depression can hold the coil portions 208a, 208b alone (e.g. with an interference fit) and/or they can be adhered within the depression. For example, the depressions can be filled with a selected epoxy or adhesive to hold the coil portions 208a, b in place.

Accordingly, both of the coil portions 208a and 208b work as a single coil to increase the electromagnetic (EM) signal from the respective coil portions 208a and 208b. It will be understood, as discussed above, that the coil portions 208a and 208b can either receive or transmit an electromagnetic field to generate the EM signal. Additionally, the coil portions 208a and 208b can be wound around a core. The core can includes an EM permeable core material or be formed around an air core, as selected, for signal strength. Further, the coil portions 208a,b can be formed of a plurality of turns of insulated wire.

A third coil 220 can be formed as a first coil portion 220a and a second coil portion 220b (not illustrated) positioned substantially 180 degrees from the first coil portion 220a around the long axis 202 of the instrument 200. Again, each of the coil portions 220a and 220b can be formed by winding a wire in a selected shape around a winding axis, such as an oval including a long radius 222 generally aligned with the long axis 202 of the instrument 200 and a short radius 224 that is generally perpendicular to the long radius 222 of the coil portion 220a. Further, each of the coil portions 220a and 220b can be positioned on a surface or in a depression formed in the surface of the outer wall 204 of the instrument 200. Further, the two coil portions 220a and 220b can be connected in series similar to the coil portions 208a and 208b to increase the EM signal or sensitivity and reduce relative size per total number of windings relative to the instrument 200. Further, the coil portions 220a,b can be formed of a plurality of turns of insulated wire.

Each of the coil portions 208a, 208b, 220a, and 220b can be positioned at a selected angle 234 from one another around the long axis 202 of the instrument 200. As illustrated in FIG. 6, the angle 224 can be a 90 degree angle formed between the coil portions 208a, 208b, 220a, and 220b and is defined as an angle 234 formed by two lines 230 and 232 that intersect at the long axis 202 of the instrument 200 and extend through the centers of two adjacent of the coil portions, such as 208a and 220a. The lines 230 and 232 can also be defined as extending perpendicular from a plan defined by an outside of the respective coil portions 202a,b and 220a,b that intersects the axis 202. The 90 degree angle is an angle 234 formed between the two lines 230 and 232. Accordingly, each of the coil portions 208a, b and 220a, b can be positioned around the long axis 202 of the instrument 200.

Further, the navigational vectors of the respective coil portions 208 and 220 will generally be along the respective lines 230 and 232. Accordingly, these two navigational vectors are generally 90 degrees relative to one another and are at different angles relative to the navigational vector that would generally be along the long axis 202 formed by the first coil 206 and near the first coil 206. It will be understood, however, that the navigation vectors from the coil portions 208 and 220 can be positioned relative to the instrument 200 by changing the angle 224 to be a angular offset of the respective coil segments (e.g. more or less than 90 degrees) and by angling the surface of the windings of the respective coil portions 208 and 220 relative to the long axis 202 of the instrument 200.

In one example, the coil portions 208 and 220 can have an end nearer the distal end 240 positioned a distance further from the axis 202 than an end further from the distal end 240, as exemplarily illustrated in phantom coil 208a'. Although, the coil portions 208 and 220 can be angled in any appropriate manner to generate a selected navigation vector relative to the instrument 200. Accordingly, the line 230 can be formed to be substantially not perpendicular to the long axis 202 of the instrument 200 to change the navigational vector of the coil portions 208. By altering the navigational vector in such a manner, the respective navigation vectors can be used to identify different positions of the respective coil segments relative to the instrument 200 for different or increased navigational accuracy.

Moreover, it will be understood that a greater number of coil portions can be positioned on the instrument 200. For example, additional oval coil portions can be positioned at different angles relative to the instrument 200, such as about 45 degrees relative to the illustrated coil portions, at a position further from the distal end 240. These additional coil portions can generate additional navigational vectors relative to the instrument 200 for increased navigational accuracy. The additional coil portions can be used for backup, error detection, location verification, and other appropriate reasons. All of the coil sets can act independently for navigation vector determination. Also, it will be understood, that the coil portions need not be at 90 degrees relative to one another.

Figure 7:
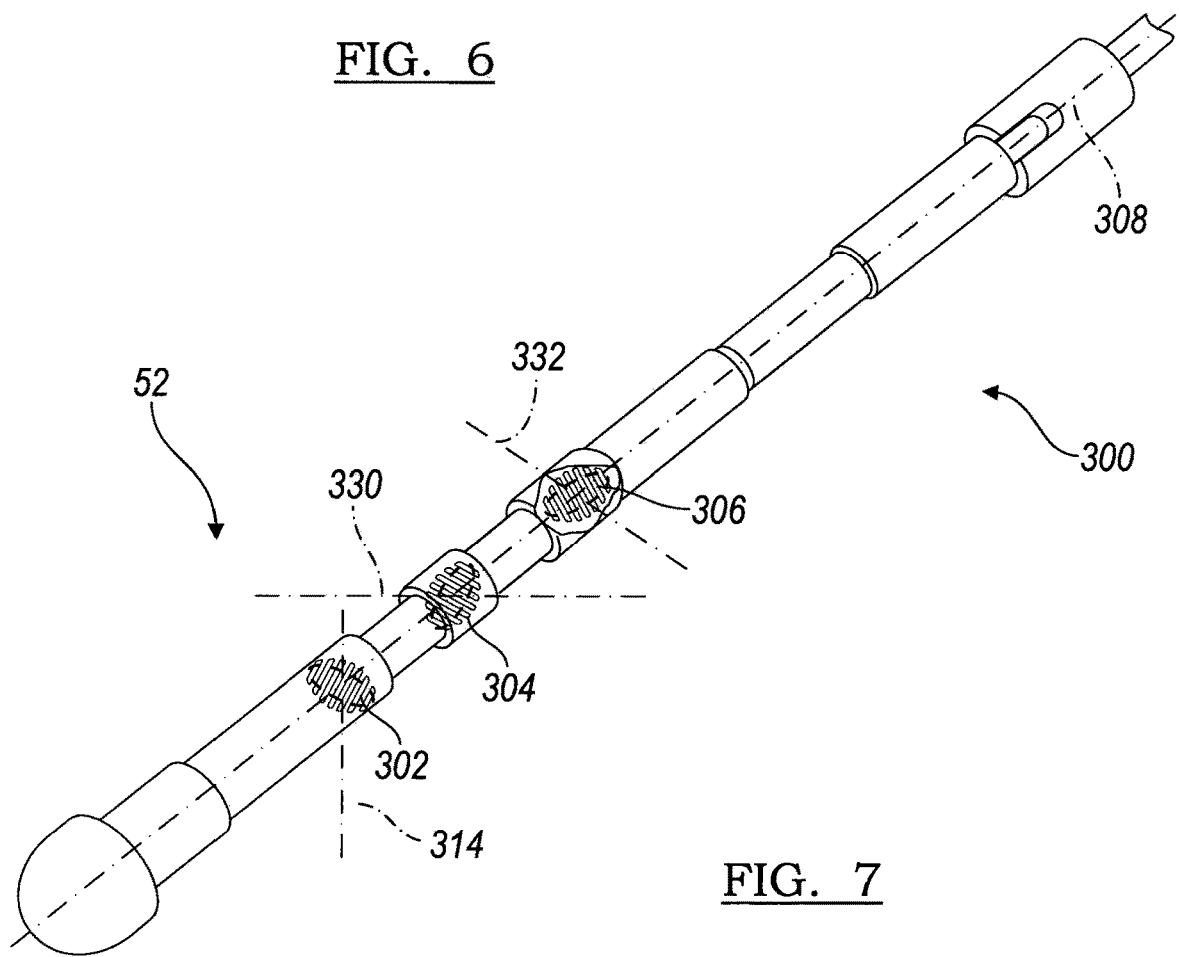
FIG. 7 is a perspective view of a tracking device on an instrument, according to various embodiments.
Figure 8:
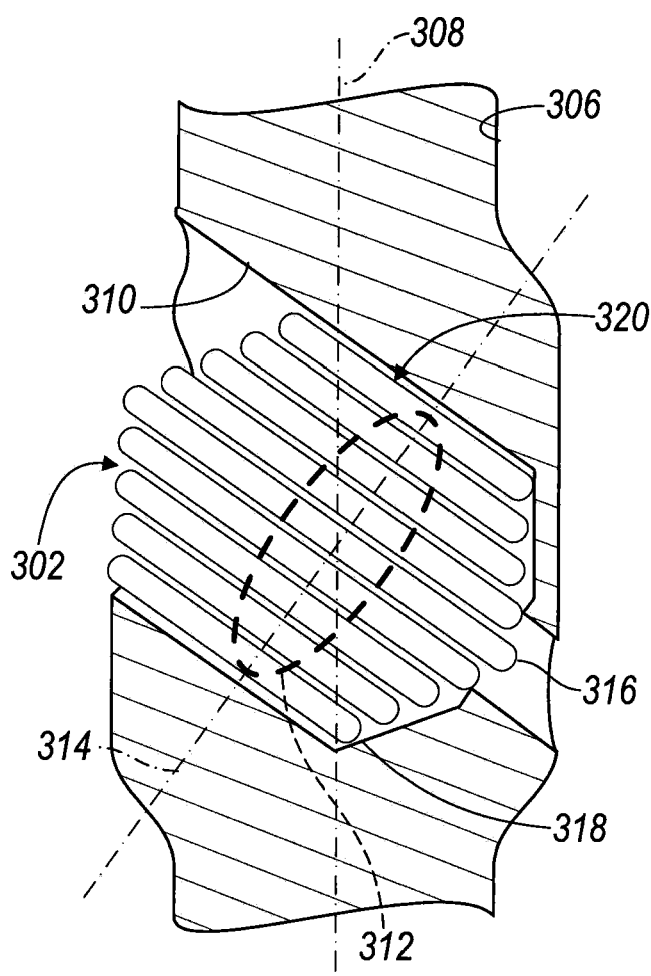
FIG. 8 is a detail perspective view of the tracking device of FIG. 7 on an instrument, according to various embodiments.

With reference to FIGS. 7 and 8, an instrument 300 according to various embodiments is illustrated. The instrument 300 can be similar to the instruments discussed above, such as a stylet, a guide tube, a drill bit, or other appropriate instrument to be moved relative to a subject, such as the patient 14. The instrument 300 can include the tracking device 52 which includes a plurality of tracking elements 302, 304, and 306. Each of the respective tracking elements 302, 304, and 306, can be positioned along a long axis 308 of the instrument 300. It will be understood, as discussed above, that more or less than three tracking elements can be provided with the instrument 300.

According to various embodiments, the tracking elements 302, 304, and 306 can be embedded or positioned within a holding portion, such as one or more recesses 310 formed in the instrument 300. The elements 302, 304 and 306 can be positioned in the recesses 310 such as by molding, machining the recess 310 and affixing the navigation portions within the recess 310, or any other appropriate configuration. The shape of the tracking elements 302, 304, and 306, as discussed herein, can include flat or planar portions that can be keyed or fit with an interference fit with the holding portion or each of the recesses 310. In addition, or alternatively to the keyed fit, the tracking elements 302, 304, and 306 can be affixed within the recesses 310 with an adhesive, such as an epoxy, to fix the tracking elements 302, 304, and 306 relative to the instrument 300.

Each of the three tracking elements 302, 304, and 306 can be formed or provided as a coil of wire wrapped around a selected core 312. The core 312 can be a highly magnetically permeable core or an air core to form each of the respective tracking elements 302-306. Generally, each of the tracking elements, such as the tracking element 302 illustrated in FIG. 8, is wrapped around the core 312 and will define a navigation vector or axis 314 that is generally aligned with an axis about which the tracking elements 302 or, the respective other tracking elements, is wrapped.

Generally the tracking element 302, or any other appropriate tracking elements, are barrel-wrapped around the core 312 such that the coil is wide near a central portion 316 and tapered towards the respective ends 318 and 320 of the respective tracking elements 302-306. The end surfaces at the respective ends 318 and 320 can generally be flat to be keyed or have an interference fit within the holding portion recesses 310. Also, the shape of the windings of the tracking elements 302-306 can generally be defined by the core 312, especially if the core 312 is a shaped material. Thus, the winding is generally around the navigation axis 314.

As specifically illustrated in FIG. 8, the coil winding wraps around the core 312 of the tracking element 302 to be small on the first end 318 wider in the center 316 and taper again to a smaller end 320. Accordingly the tracking element 302 can generally or roughly define a barrel shape to be positioned within or on the instrument 300 in a selected or indexed manner. The barrel shape generally has flatter or flattened ends so that its orientation is maintained and can be selected relative to the instrument 300. It will be understood that a core can be selected to include the barrel shape of the winding of the wire can form the barrel shape. It is also understood that a barrel shape is not necessary and other shapes can be selected. Also, a core shape can be selected to index or be fit fixedly within the recesses 310.

The appropriate plurality of navigation vectors can provide the instrument 300 with a six degree of freedom tracking device 52 as each of the coil elements can be positioned such that their respective navigation vectors 314, 330, and 332, are positioned substantially orthogonal relative to one another along the longitudinal length of the long axis 302 of the instrument 300. Although, it is understood that three different vectors are not required to obtain the six degree of freedom information, as discussed above. By providing the plurality of navigational vectors or axes of winding of the tracking elements 302-306 (e.g. indexing or fixing the tracking elements 302-306 at different angles relative to the instrument 300), a plurality of vectors can be identified for the instrument 300 using each of the individual tracking elements 302-306. Accordingly, the instrument 300 can be navigated with substantially six degrees of freedom of location information determining location information of each of the respective tracking elements 302-306. However, each of the coil elements need not be overlapping one another and can be positioned at any appropriate location within the instrument 300.

Additionally, it will be understood, that each of the tracking elements 302-306 can be positioned at any appropriate location relative to the instrument 300 or any other appropriate instrument. Accordingly, having the plurality of tracking elements 302-306 as substantially next to one another, as illustrated in FIG. 7, is not required and they can be spaced apart for various reasons. For example, communication lines, such as to an ablation electrode, may pass between the respective tracking elements 302-306 and the spacing may be altered for such considerations. However, knowing the location of the respective tracking elements 302-306 relative to each other and the instrument 300 allows for navigation of the instrument 300 with substantially six degrees of freedom with the navigation system 10.

Figure 9:
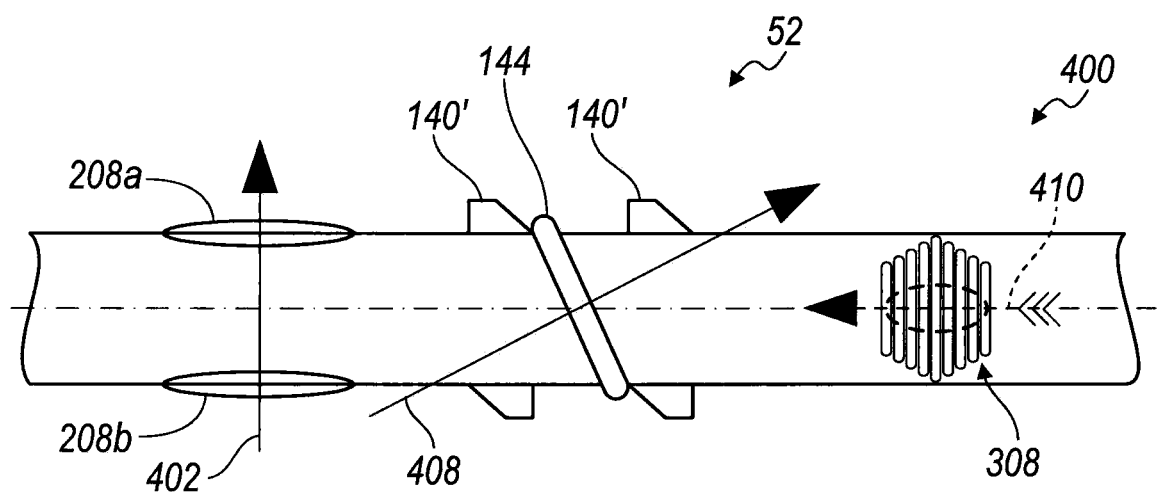
FIG. 9 is a plan view of an instrument with a tracking device, according to various embodiments.

It will be understood that various instruments, especially the instruments 100, 200, and 300, are illustrated herein for examples. However, a plurality of instruments can include all or individually the various tracking devices or portions thereof illustrated in particular embodiments. For example, as illustrated in FIG. 9, an instrument 400, according to various embodiments, can include one or more of each of the selected portions of the tracking device 52. Accordingly, the tracking device 52 can include oval coil segments 208a and 208b connected in series on the instrument 400. Additionally, an angled coil, such as the coil configuration 144 can be provided between guide posts 140' on the instrument 400. Additionally, a coil element, such as the coil element 308 can be provided within the instrument 400. Each of the respective coil elements can include navigation vectors that are positioned at different angles relative to one another, such as substantially orthogonally or otherwise non-aligned. For example, the coil elements 208a, b can define a navigation vector 402 that can be perpendicular to a long axis 406 of the instrument 400. The coil winding 144 can define a navigation vector 408 at a selected angle relative to the long axis 406. Finally, the coil element 308 can define a third navigation vector 410 relative to the long axis 406 that can also be generally perpendicular, but in the opposite or different direction of the coil elements 208a, 208b or aligned with the long axis. Accordingly, each of the three coil portions or segments can be positioned on the instrument 400 where each have different configurations, as discussed above, while providing a plurality of navigation vectors relative to the instrument 400. Accordingly, it will be understood that the instrument 400, according to various embodiments, need not include a substantially consistent coil segment design and can be provided for different coil segment configurations.

It will be understood that the tracking device 52 can be positioned on an instrument that is substantially not rigid. For example, the instrument can be movable or bendable and have portions that rotate relative to other portions of the instrument. Also, the tracking device 52 can be positioned on a probe that can be angled and rotated relative to the patient 14, or any appropriate subject. Accordingly, the rotational direction and orientation relative to the subject along with its three-dimensional position can be determined. Additionally, the tracking device 52 can be positioned on a substantially continuously rotating instrument, such as a drill bit, to be moved relative to the subject, such as the patient 14, and the location and other position and orientation information can be determined in the navigation system 10. Accordingly, providing the tracking device 52 and a guide tube or probe or substantially slow-moving instrument is not required, and the tracking device 52 can be placed on any appropriate instrument for navigation in the navigation system 10. For example, the elements of the tracking device 52 can be assembled and the tracking device assembly can be attached to a handle of the instrument 100, 200, 300 and 400.

The tracking devices, according to any embodiments discussed above, can be provided directly on instruments as illustrated above. It will be understood, however, that the tracking devices can be provided on other portions or members that can be interconnected or attached to any appropriate instrument. For example, as illustrated in FIG. 1, the tracking device 52 can be connected with a stem or pedestal to instrument to track the instrument. Accordingly the tracking device can be positioned on an instrument that is not originally formed with instrument so that the instrument can include the tracking device.

Additionally, the tracking devices can be provided to minimize or maintain an outer diameter or perimeter of the instrument. Although the cross section of the instrument can be provided in any selected shape (e.g. round, square, oval), the tracking devices can be provided to minimize an increase in an outer perimeter dimension, such as a diameter, due to the positioning of a tracking device on the instrument. For example, the tracking device including the coil 110, as illustrated in FIG. 2 with the instrument 100, can be wrapped around the instrument to be substantially maintained within an outer diameter of the instrument 100. As illustrated in FIG. 6, coil portions 208 and 220 can be positioned within depressions in the instrument 200 to assist in substantially maintaining an outer diameter of the instrument 200. In addition, these coil segments 208 and 220 can be made relatively flat (e.g. having a height of less than about 1 mm, including about 0.1 mm to about 1.0 mm) relative to the instrument 200 to assist in maintaining an outer diameter of the instrument 200 after positioning the coil segments relative to the instrument 200. Further, the tracking device portions 302, 304, and 306 illustrated in FIGS. 6 and 7 can be positioned on the instrument 300 substantially within an outer diameter of the instrument 300. In particular, the tracking portions can be embedded within an outer diameter of instrument 300 to maintain the size of the instrument 300 for various purposes. Accordingly, the tracking devices, according to the various embodiments, can be connected with instruments to assist in maintaining a dimension of the instrument for purposes of assisting in minimizing the size of instrument for surgical procedures. It will be also understood that the tracking devices can interconnected with other instruments to assist in tracking instruments for nonsurgical procedures, such as manufacturing, exploration, and other purposes.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A navigation system comprising:
   an instrument that is operable to be moved relative to a subject and comprises
      an exterior wall, wherein the exterior wall is cylindrical-shaped and defines a through bore along a longitudinal axis,
      a first series of guide posts, wherein each of the first series of guide posts extends radially from the exterior wall, wherein first series of guide posts are spaced apart from each other to provide first gaps between consecutive ones of the first series of guide posts,
      a second series of guide posts corresponding respectively to the first series of guide posts and on an opposite side of the exterior wall as the first series of guide posts, wherein at least some of the second series of guide posts are offset axially along the longitudinal axis relative to the corresponding ones of the first series of guide posts, wherein the second series of guide posts are spaced apart from each other to provide second gaps between consecutive ones of the second series of guide posts, and
      at least one tracking device positioned on the exterior wall and comprising a first coil defining a first navigation vector and including a first wire wrapped around the exterior wall and in contact with (i) a first guide post of the first series of guide posts, and (ii) a first guide post of the second series of guide posts, wherein
         a first end of the first coil is disposed in one of the first gaps and between the first guide post and a second guide post of the first series of guide posts,
         a second end of the first coil is disposed in one of the second gaps and between the first guide post and a second guide post of the second series of guide posts,
         a third gap exists between the first end of the first coil and the second guide post of the first series of guide posts, such that the first end of the first coil is not in contact with the second guide post of the first series of guide posts when the exterior wall is in a non-bent state,
         a fourth gap exists between the second end of the first coil and the second guide post of the second series of guide posts, such that the second end of the first coil is not in contact with the second guide post of the second series of guide posts when the exterior wall is in the non-bent state,
         the third gap and the fourth gap are void of any coil windings such that no winding of a coil is wound through the third gap and the fourth gap,
         while the instrument is being bent in a first direction, the third gap decreases in size, and
         while the instrument is being bent in a second direction, the fourth gap decreases in size;
   a navigation processor operable to receive a signal indicative of the first navigation vector and determine a position of the instrument based on the first navigation vector; and
   a display device operable to display the determined position.

2. The navigation system of claim 1, wherein:
   the at least one tracking device comprises a second coil defining a second navigation vector and including a second wire wrapped around the exterior wall and in contact with (i) a second guide post of the first series of guide posts, and (ii) a second guide post of the second series of guide posts;
   a first end of the second coil is disposed in a second one of the first gaps and between a third guide post and a fourth guide post of the first series of guide posts;
   a second end of the second coil is disposed in a second one of the second gaps and between a third guide post and a fourth guide post of the second series of guide posts;
   the first coil contacts a first guide wall of one of the first series of guide posts;
   the second coil contacts a second guide wall of one of the second series of guide posts;
   angles of the first guide wall and the second guide wall relative to the longitudinal axis are different from one another; and
   the first navigation vector and the second navigation vector are at different angles relative to the longitudinal axis.

3. The navigation system of claim 2, further comprising:
   an imaging system operable to generate image data regarding the subject; and
   a localizer operable to generate an electromagnetic field,
   wherein the display device is operable to display an image of the subject based on the generated image data, and
   wherein the first navigation vector and the second navigation vector are based on a sensed electromagnetic field.

4. The navigation system of claim 2, wherein:
   the first coil contacts a support wall of a second one of the second series of guide posts;
   the second coil contacts a support wall of a second one of the first series of guide posts;
   the guide wall of the one of the first series of guide posts and the guide wall of the one of the second series of guide posts are at acute angles relative to the longitudinal axis; and
   the support wall of the second one of the second series of guide posts and the support wall of the second one of the first series of guide posts extend in directions normal to the longitudinal axis.

5. The navigation system of claim 2, wherein each of the first wire and the second wire are electrically insulated from one another.

6. The system according to claim 1, wherein:
   the guide posts of the first series of guide posts have respective first outer walls;
   the guide posts of the second series of guide posts have respective second outer walls; and the first outer walls and the second outer walls extend parallel to the exterior wall.

7. An instrument comprising:
an exterior wall defining a longitudinal axis and operable to be moved relative to a subject;
a first series of guide posts extending radially from the exterior wall, wherein each of the first series of guide posts are spaced apart from each other to provide first gaps between consecutive ones of the first series of guide posts;
a second series of guide posts corresponding respectively to the first series of guide posts and on an opposite side of the exterior wall as the first series of guide posts, wherein at least some of the second series of guide posts are offset axially along the longitudinal axis relative to the corresponding ones of the first series of guide posts, and wherein second series of guide posts are spaced apart from each other to provide second gaps between consecutive ones of the second series of guide posts; and
a first conductive wire wound around the exterior wall of the instrument to provide a first coil,
wherein
the first coil defines a first navigation vector,
the first conductive wire is in contact with (i) a first guide post of the first series of guide posts, and (ii) a first guide post of the second series of guide posts,
a first end of the first coil is disposed in one of the first gaps and between the first guide post and a second guide post of the first series of guide posts,
a second end of the first coil is disposed in one of the second gaps and between the first guide post and a second guide post of the second series of guide posts,
a third gap exists between the first end of the first coil and the second guide post of the first series of guide posts, such that the first end of the first coil is not in contact with the second guide post of the first series of guide posts when the exterior wall is in a non-bent state,
a fourth gap exists between the second end of the first coil and the second guide post of the second series of guide posts, such that the second end of the first coil is not in contact with the second guide post of the second series of guide posts when the exterior wall is in the non-bent state,
the third gap and the fourth gap are void of any coil windings such that no winding of a coil is wound through the third gap and the fourth gap,
while the instrument is being bent in a first direction, the third gap decreases in size, and
while the instrument is being bent in a second direction, the fourth gap decreases in size.

8. A navigation system comprising:
the instrument of claim 7; and
a localizer operable to generate an electromagnetic field, wherein
the first conductive wire is configured to sense the electromagnetic field, and
the first navigation vector is defined by current induced in the first conductive wire by the electromagnetic field.

9. The instrument of claim 7, wherein:
the guide posts of the first series of guide posts have respective first outer walls;
the guide posts of the second series of guide posts have respective second outer walls; and
the first outer walls and the second outer walls extend parallel to the exterior wall.

10. A method of manufacturing an instrument having a longitudinal axis, wherein the instrument is operable to be moved relative to a subject, the method comprising:
forming a flexible exterior wall, wherein the exterior wall defines a through bore and the longitudinal axis;
forming a first series of guide posts on and extending radially from the exterior wall, wherein each of the first series of guide posts are spaced apart from each other to provide first gaps between consecutive ones of the first series of guide posts;
forming a second series of guide posts corresponding respectively to the first series of guide posts and on an opposite side of the exterior wall as the first series of guide posts, wherein at least some of the second series of guide posts are offset axially along the longitudinal axis relative to the corresponding ones of the first series of guide posts, and wherein the second series of guide posts are spaced apart from each other to provide second gaps between consecutive ones of the second series of guide posts; and
wrapping a first conductive wire around the exterior wall to provide a first coil, wherein the first coil defines a first navigation vector,
wherein
the first conductive wire is in contact with (i) a first guide post of the first series of guide posts, and (ii) a first guide post of the second series of guide posts,
a first end of the first coil is disposed in one of the first gaps and between the first guide post and a second guide post of the first series of guide posts,
a second end of the first coil is disposed in one of the second gaps and between the first guide post and a second guide post of the second series of guide posts,
a third gap exists between the first end of the first coil and the second guide post of the first series of guide posts, such that the first end of the first coil is not in contact with the second guide post of the first series of guide posts when the exterior wall is in a non-bent state,
a fourth gap exists between the second end of the first coil and the second guide post of the second series of guide posts, such that the second end of the first coil is not in contact with the second guide post of the second series of guide posts when the exterior wall is in the non-bent state,
the third gap and the fourth gap are void of any coil windings such that no winding of a coil is wound through the third gap and the fourth gap,
while the instrument is being bent in a first direction, the third gap decreases in size, and
while the instrument is being bent in a second direction, the fourth gap decreases in size.

11. The method of claim 10, wherein:
the guide posts of the first series of guide posts have respective guide walls;
the guide posts of the second series of guide posts have respective guide walls; and
the guide walls of the first series of guide posts and the guide walls of the second series of guide posts are at acute angles relative to the longitudinal axis.

12. The method of claim 11, wherein:
the guide walls of the first series of guide posts extend parallel to one another; and
the guide walls of the second series of guide posts extend parallel to one another.

13. The method of claim 10, further comprising:
tracking the instrument relative to the subject;
receiving a signals from the first coil and a second coil of the instrument, wherein the received signals are indicative of the first navigation vector and a second navigation vector of the second coil;
executing instructions via a navigation processor to determine location information of the instrument based on the received signals, wherein the determining of the location information includes determining at least six degrees of freedom of location information of the instrument; and
displaying the at least six degrees of freedom of location information.

14. The method of claim 10, wherein wrapping the first conductive wire around the exterior wall includes wrapping the first conductive wire around the exterior wall a plurality of times between the first guide post and the second guide post of the first series of guide posts.

15. The instrument of claim 7, wherein:
the guide posts of the first series of guide posts have respective first guide walls;
the guide posts of the second series of guide posts have respective second guide walls; and
the first guide walls and the second guide walls are semicircular-shaped.

16. The navigation system of claim 1, wherein each of the first series of guide posts and the second series of guide posts are frustroconical-shaped.

17. The navigation system of claim 1, wherein a base of each of the first series of guide posts and the second series of guide posts is attached to the exterior wall and is circular-shaped.

18. The navigation system of claim 1, wherein:
each of the first series of guide posts and the second series of guide posts comprises an outer wall and a slanted and curved guide wall, wherein each of the outer walls is disposed radially outward from the exterior wall; and
the slanted and curved guide wall of each of the first series of guide posts and the second series of guide posts extends in a longitudinal direction and at an acute angle from an exterior surface of the exterior wall to the corresponding one of the outer walls.

19. The navigation system of claim 18, wherein:
the slanted and curved guide wall of the first guide post of the first series of guide posts is in contact with the first coil;
the first guide post of the first series of guide posts comprises a support wall;
the support wall of the first guide post of the first series of guide posts extends perpendicular to the longitudinal axis and is in contact with the first coil;
the first guide post of the second series of guide posts comprises a support wall; and
the support wall of the first guide posts of the second series of guide posts extends perpendicular to the longitudinal axis and is in contact with the first coil.

20. The navigation system of claim 19, wherein:
the second guide post of the first series of guide posts is not in contact with the first coil;
the second guide post of the second series of guide posts is not in contact with a second coil; and
the second coil is wrapped on the exterior wall.

21. The method of claim 10, further comprising wrapping a second conductive wire around the exterior wall to provide a second coil, wherein:
the second conductive wire is in contact with (i) a third guide post of the first series of guide posts, and (ii) a third guide post of the second series of guide posts,
a first end of the second coil is disposed in a second one of the first gaps and between the third guide post and a fourth guide post of the first series of guide posts,
a second end of the second coil is disposed in a second one of the second gaps and between the third guide post and a fourth guide post of the second series of guide posts.

22. A method of operating an instrument and determining location information for a tracking device of the instrument relative to a subject, wherein the instrument comprises an exterior wall having a longitudinal axis, a first series of guide posts, a second series of guide posts, and the tracking device, wherein the first series of guide posts extend radially from the exterior wall and are spaced apart from each other to provide first gaps between consecutive ones of the first series of guide posts, wherein the second series of guide posts extends radially from the exterior wall, wherein the second series of guide posts are spaced apart from each other to provide second gaps between consecutive ones of the second series of guide posts, and wherein the tracking device is positioned on the exterior wall of the instrument and includes a first coil, the method comprising:
generating an electromagnetic field via a localizer;
permitting the instrument to bend in a first direction and in a second direction;
detecting the electromagnetic field via the first coil while the instrument is bent in the first direction and is bent in the second direction, wherein the first coil defines a first navigation vector and is in contact with (i) a first guide post of the first series of guide posts, and (ii) a first guide post of the second series of guide posts, wherein a first end of the first coil is disposed in one of the first gaps, wherein a second end of the first coil is disposed in one of the second gaps, wherein a third gap exists between the first end of the first coil and the second guide post of the first series of guide posts, such that the first end of the first coil is not in contact with the second guide post of the first series of guide posts when the exterior wall is in a non-bent state, wherein a fourth gap exists between the second end of the first coil and the second guide post of the second series of guide posts, such that the second end of the first coil is not in contact with the second guide post of the second series of guide posts when the exterior wall is in the non-bent state, wherein the third gap and the fourth gap are void of any coil windings such that no winding of a coil is wound through the third gap and the fourth gap, wherein while the instrument is being bent in the first direction, the third gap decreases in size, and wherein while the instrument is being bent in the second direction, the fourth gap decreases in size;
generating a first signal via the first coil based on the electromagnetic field, wherein the first coil is wrapped around a first axis of rotation and defines a navigation vector, and wherein the first signal corresponds to the navigation vector; and
executing instructions to determine a plurality of degrees of freedom of location information for the instrument based on the first signal.

23. The method of claim 22, further comprising:
receiving the first signal from the tracking device as the instrument is moved relative to the subject;
determining a location of the instrument relative to the subject based on the first signal; and displaying a representation of the determined location of the instrument relative to the subject on a display.

24. The method of claim 23, further comprising:
detecting the electromagnetic field via a second coil and a third coil, wherein the second coil is wrapped around the exterior wall and a second axis of rotation, wherein the third coil is wrapped around the exterior wall and a third axis of rotation, wherein the first axis of rotation, the second axis of rotation and the third axis of rotation are at different angles relative to the longitudinal axis;
generating a second signal via the second coil based on the electromagnetic field;
generating a third signal via the third coil based on the electromagnetic field;
receiving the second signal and the third signal from the tracking device as the instrument is moved relative to the subject; and
determining the location of the instrument relative to the subject based on the second signal and the third signal.

25. The navigation system of claim 1, wherein while the exterior wall is being bent one or more of the first series of guide posts and one or more of the second series of guide posts move relative to other ones of the first series of guide posts and other ones of the second series of guide posts.

26. The navigation system of claim 1, wherein:
the one of the first gaps allows the instrument to bend a first certain amount in the first direction without the first end of the first coil contacting both the first guide post and the second guide post of the first series of guide posts at a same time, and
the one of the second gaps allows the instrument to bend a second certain amount in the second direction without the second end of the first coil contacting both the first guide post and the second guide post of the second series of guide posts at a same time.

27. The navigation system of claim 26, wherein:
the at least one tracking device comprises a second coil defining a second navigation vector and including a second wire wrapped around the exterior wall and in contact with (i) a second guide post of the first series of guide posts, and (ii) a second guide post of the second series of guide posts;
a first end of the second coil is disposed in a second one of the first gaps and between a third guide post and a fourth guide post of the first series of guide posts;
a second end of the second coil is disposed in a second one of the second gaps and between a third guide post and a fourth guide post of the second series of guide posts;
the second one of the first gaps allows the instrument to bend the first certain amount in the first direction without the first end of the second coil contacting both the third guide post and the fourth guide post of the first series of guide posts at a same time;
the second one of the second gaps allows the instrument to bend the second certain amount in the second direction without the second end of the second coil contacting both the third guide post and the fourth guide post of the second series of guide posts at a same time;
the first coil contacts a first guide wall of one of the first series of guide posts;
the second coil contacts a second guide wall of one of the second series of guide posts;
angles of the first guide wall and the second guide wall relative to the longitudinal axis are different from one another; and the first navigation vector and the second navigation vector are at different angles relative to the longitudinal axis.

28. The navigation system of claim 1, wherein:
the first end of the first coil is in contact with the first guide post of the first series of guide posts when the exterior wall is in the non-bent state; and
the second end of the first coil is in contact with the first guide post of the second series of guide posts when the exterior wall is in the non-bent state.

29. The instrument of claim 7, wherein:
the one of the first gaps allows the exterior wall to bend a first certain amount in the first direction without the first end of the first coil contacting both the first guide post and the second guide post of the first series of guide posts at a same time; and
the one of the second gaps allows the exterior wall to bend a second certain amount in the second direction without the second end of the first coil contacting both the first guide post and the second guide post of the second series of guide posts at a same time.

30. The method of claim 10, wherein:
the one of the first gaps allows the instrument to bend a first certain amount in the first direction without the first end of the first coil contacting both the first guide post and the second guide post of the first series of guide posts at a same time; and
the one of the second gaps allows the instrument to bend a second certain amount in the second direction without the second end of the first coil contacting both the first guide post and the second guide post of the second series of guide posts at a same time.

31. The method of claim 30, further comprising wrapping a second conductive wire around the exterior wall to provide a second coil, wherein:
the second conductive wire is in contact with (i) a third guide post of the first series of guide posts, and (ii) a third guide post of the second series of guide posts;
a first end of the second coil is disposed in a second one of the first gaps and between the third guide post and a fourth guide post of the first series of guide posts;
a second end of the second coil is disposed in a second one of the second gaps and between the third guide post and a fourth guide post of the second series of guide posts;
the second one of the first gaps allows the instrument to bend the first certain amount in the first direction without the first end of the second coil contacting both the third guide post and the fourth guide post of the first series of guide posts at a same time; and
the second one of the second gaps allows the instrument to bend the second certain amount in the second direction without the second end of the second coil contacting both the third guide post and the fourth guide post of the second series of guide posts at a same time.

32. The method of claim 22, wherein:
the one of the first gaps allows the instrument to bend a first certain amount in the first direction without the first end of the first coil contacting both the first guide post and a second guide post of the first series of guide posts at a same time; and
the one of the second gaps allows the instrument to bend a second certain amount in the second direction without the second end of the first coil contacting both the first guide post and the second guide post of the second series of guide posts at a same time.

33. The navigation system of claim 1, wherein a base of each of the first series of guide posts and the second series of guide posts is attached to the exterior wall and is rounded.

34. The navigation system of claim 1, wherein an axis of curvature of a base of each of the first series of guide posts extends radially from the longitudinal axis.

35. The navigation system of claim 1, wherein:
the first end of the first coil is a first portion of the first coil disposed between the first guide post and the second guide post of the first series of guide posts; and
the second end of the first coil is a second portion of the first coil disposed between the first guide post and the second guide post of the second series of guide posts.

36. The navigation system of claim 35, wherein:
the first coil includes the first portion of the first coil, the second portion of the first coil, and a remaining portion of the first coil; and
the remaining portion of the first coil is (i) disposed circumferentially along the exterior wall between the first portion and the second portion, (ii) not disposed between the first guide post and the second guide post of the first series of guide posts, and (iii) not disposed between the first guide post and the second guide post of the second series of guide posts.

37. The navigation system of claim 1, wherein:
the first coil consists of the first end of the first coil, the second end of the first coil and a center portion;
the first end of the first coil is disposed between the first guide post and the second guide post of the first series of guide posts;
the second end of the first coil is disposed between the first guide post and the second guide post of the second series of guide posts; and
the center portion of the first coil is (i) disposed circumferentially along the exterior wall between the first end and the second end, (ii) not disposed between the first guide post and the second guide post of the first series of guide posts, and (iii) not disposed between the first guide post and the second guide post of the second series of guide posts.

38. The navigation system of claim 1, wherein:
the first end of the first coil is defined as a whole portion of the first coil disposed between the first guide post and the second guide post of the first series of guide posts; and
the second end of the first coil is defined as a whole portion of the first coil disposed between the first guide post and the second guide post of the second series of guide posts.

39. The navigation system of claim 1, wherein the first series of guide posts comprises at least three guide posts.

40. The navigation system of claim 1, wherein the first series of guide posts comprises at least four guide posts.

41. The navigation system of claim 27, wherein:
the first guide wall of the first guide post of the first series of guide posts extends radially outward from the exterior wall and is not at an acute angle relative to the exterior wall; and
the second guide wall of the second guide post of the second series of guide posts extends radially outward from the exterior wall and is at an obtuse angle relative to the exterior wall.

42. The navigation system of claim 1, wherein an axis of curvature of at least one of a perimeter or a circumferential edge of a base of each of the first series of guide posts extends radially from the longitudinal axis.

43. The navigation system of claim 1, wherein:
each of the first series of guide posts has a base; and
axes of curvature of circumferential edges of the bases of the first series of guide posts extend radially from the longitudinal axis through respective centers of the bases of the first series of guide posts in directions orthogonal to respective radii of the bases of the first series of guide posts.

* * * * *